US008644931B2

(12) United States Patent
Stadler et al.

(10) Patent No.: US 8,644,931 B2
(45) Date of Patent: Feb. 4, 2014

(54) IMPEDANCE VARIABILITY ANALYSIS TO IDENTIFY LEAD-RELATED CONDITIONS

(75) Inventors: Robert W. Stadler, Shoreview, MN (US); Bruce D. Gunderson, Plymouth, MN (US); Amisha S. Patel, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1262 days.

(21) Appl. No.: 12/180,304

(22) Filed: Jul. 25, 2008

(65) Prior Publication Data

US 2009/0299432 A1 Dec. 3, 2009

Related U.S. Application Data

(60) Provisional application No. 61/058,153, filed on Jun. 2, 2008.

(51) Int. Cl.
*A61N 1/00* (2006.01)

(52) U.S. Cl.
USPC ................................ 607/28; 607/27

(58) Field of Classification Search
USPC ..................... 607/28, 7–8; 600/547
See application file for complete search history.

(56) References Cited

U.S. PATENT DOCUMENTS

| | | | |
|---|---|---|---|
| 4,140,131 A | 2/1979 | Dutcher et al. |
| 4,374,382 A | 2/1983 | Markowitz |
| 4,428,378 A | 1/1984 | Anderson et al. |
| 4,549,548 A | 10/1985 | Wittkampf et al. |
| 4,825,869 A | 5/1989 | Sasmor et al. |
| 4,860,749 A | 8/1989 | Lehmann |
| 4,899,750 A | 2/1990 | Ekwall |
| 4,913,146 A | 4/1990 | DeCote, Jr. |
| 4,944,746 A | 7/1990 | Iwata et al. |
| 5,003,975 A | 4/1991 | Hafelfinger et al. |
| 5,107,833 A | 4/1992 | Barsness |
| 5,117,824 A | 6/1992 | Keimel et al. |

(Continued)

FOREIGN PATENT DOCUMENTS

| | | |
|---|---|---|
| EP | 1857141 A | 11/2007 |
| WO | WO02/18009 A1 | 3/2002 |
| WO | WO2005/056109 A | 6/2005 |

OTHER PUBLICATIONS

Danilovic et al, "Pacing Impedance Variability in Tined Steroid Eluting Leads" Jul. 1, 1998, pp. 1356-1363, vol. 21, No. 7, Malden, MA, US.

(Continued)

*Primary Examiner* — Christopher D Koharski
*Assistant Examiner* — Catherine Voorhees
(74) *Attorney, Agent, or Firm* — Michael J. Ostrom

(57) ABSTRACT

In general, the disclosure relates to techniques for calculating mean impedance values and impedance variability values to detect a possible condition with a lead or device-lead pathway or connection. In one example, a device may be configured to determine an impedance value for an electrical path based on a plurality of measured impedance values for the electrical path, wherein the electrical path comprises a plurality of electrodes, and to determine an impedance variability value based on at least one of the plurality of measured impedance values. The device may be further configured to determine a threshold value based on the determined impedance value and the impedance variability value, compare a newly measured impedance value for the electrical path to the threshold value, and indicate a possible condition of the electrical path based on the comparison.

42 Claims, 12 Drawing Sheets

(56) References Cited

U.S. PATENT DOCUMENTS

| | | |
|---|---|---|
| 5,137,021 A | 8/1992 | Wayne et al. |
| 5,168,871 A | 12/1992 | Grevious |
| 5,184,614 A | 2/1993 | Collins et al. |
| 5,193,535 A | 3/1993 | Bardy et al. |
| 5,201,865 A | 4/1993 | Kuehn |
| 5,215,081 A | 6/1993 | Ostroff |
| 5,224,475 A | 7/1993 | Berg et al. |
| 5,226,415 A | 7/1993 | Girodo et al. |
| 5,292,343 A | 3/1994 | Blanchette et al. |
| 5,312,441 A | 5/1994 | Mader et al. |
| 5,314,450 A | 5/1994 | Thompson |
| 5,324,315 A | 6/1994 | Grevious |
| 5,354,319 A | 10/1994 | Wyborny et al. |
| 5,381,803 A | 1/1995 | Herleikson et al. |
| 5,383,909 A | 1/1995 | Keimel |
| 5,411,530 A | 5/1995 | Akhtar |
| 5,431,692 A | 7/1995 | Hansen et al. |
| 5,462,060 A | 10/1995 | Jacobson et al. |
| 5,507,746 A | 4/1996 | Lin |
| 5,507,786 A | 4/1996 | Morgan et al. |
| 5,534,018 A | 7/1996 | Wahlstrand et al. |
| 5,545,183 A | 8/1996 | Altman |
| 5,545,186 A | 8/1996 | Olson et al. |
| 5,549,646 A | 8/1996 | Katz et al. |
| 5,558,098 A | 9/1996 | Fain |
| 5,564,434 A | 10/1996 | Halperin et al. |
| 5,660,183 A | 8/1997 | Chiang et al. |
| 5,707,398 A | 1/1998 | Lu |
| 5,722,997 A | 3/1998 | Nedungadi et al. |
| 5,730,141 A | 3/1998 | Fain et al. |
| 5,741,311 A | 4/1998 | Mc Venes et al. |
| 5,749,907 A | 5/1998 | Mann |
| 5,755,735 A | 5/1998 | Richter et al. |
| 5,755,736 A | 5/1998 | Gillberg et al. |
| 5,755,742 A | 5/1998 | Schuelke et al. |
| 5,776,168 A | 7/1998 | Gunderson |
| 5,814,088 A | 9/1998 | Paul et al. |
| 5,868,793 A | 2/1999 | Nitzsche et al. |
| 5,891,170 A | 4/1999 | Nitzsche et al. |
| 5,891,179 A | 4/1999 | Er et al. |
| 5,897,577 A | 4/1999 | Cinbis et al. |
| 5,910,156 A | 6/1999 | Cinbis et al. |
| 5,944,746 A | 8/1999 | Kroll |
| 6,067,473 A | 5/2000 | Greeninger et al. |
| 6,070,097 A | 5/2000 | Kreger et al. |
| 6,085,118 A | 7/2000 | Hirschberg et al. |
| 6,112,119 A | 8/2000 | Schuelke et al. |
| 6,129,746 A | 10/2000 | Levine et al. |
| 6,141,585 A | 10/2000 | Prutchi et al. |
| 6,155,267 A | 12/2000 | Nelson |
| 6,169,923 B1 | 1/2001 | Kroll |
| 6,266,554 B1 | 7/2001 | Hsu et al. |
| 6,317,632 B1 | 11/2001 | Krig et al. |
| 6,317,633 B1 | 11/2001 | Jorgenson et al. |
| 6,434,428 B1 | 8/2002 | Sloman et al. |
| 6,445,952 B1 | 9/2002 | Manrodt et al. |
| 6,477,417 B1 | 11/2002 | Levine |
| 6,493,586 B1 | 12/2002 | Stahmann et al. |
| 6,629,931 B1 | 10/2003 | Begemann et al. |
| 6,650,931 B1 | 11/2003 | McClure et al. |
| 6,658,294 B1 | 12/2003 | Zadeh et al. |
| 6,721,600 B2 | 4/2004 | Jorgenson et al. |
| 6,760,624 B2 | 7/2004 | Anderson et al. |
| 6,788,971 B1 | 9/2004 | Sloman et al. |
| 6,865,141 B2 | 3/2005 | Tada et al. |
| 7,047,083 B2 | 5/2006 | Gunderson et al. |
| 7,167,747 B2 | 1/2007 | Gunderson et al. |
| 7,236,828 B2 | 6/2007 | Casavant et al. |
| 7,266,409 B2 | 9/2007 | Gunderson |
| 7,289,851 B2 | 10/2007 | Gunderson et al. |
| 7,333,855 B2 | 2/2008 | Gunderson et al. |
| 7,369,893 B2 | 5/2008 | Gunderson |
| 7,539,540 B2 | 5/2009 | Gunderson et al. |
| 7,567,835 B2 | 7/2009 | Gunderson et al. |
| 7,567,840 B2 * | 7/2009 | Armstrong ...................... 607/27 |
| 7,899,535 B2 * | 3/2011 | Bohn et al. ...................... 607/27 |
| 2001/0031997 A1 | 10/2001 | Lee |
| 2001/0037366 A1 | 11/2001 | Webb et al. |
| 2002/0091333 A1 | 7/2002 | Hsu et al. |
| 2002/0116031 A1 | 8/2002 | Vonk |
| 2002/0118215 A1 | 8/2002 | Ball et al. |
| 2002/0120307 A1 | 8/2002 | Jorgenson et al. |
| 2003/0074026 A1 | 4/2003 | Thompson et al. |
| 2003/0204215 A1 | 10/2003 | Gunderson et al. |
| 2004/0015197 A1 | 1/2004 | Gunderson |
| 2004/0064161 A1 | 4/2004 | Gunderson et al. |
| 2004/0088018 A1 | 5/2004 | Sawchuk et al. |
| 2004/0106955 A1 | 6/2004 | Swerdlow et al. |
| 2004/0122487 A1 | 6/2004 | Hatlestad et al. |
| 2004/0172080 A1 | 9/2004 | Stadler et al. |
| 2004/0186388 A1 | 9/2004 | Gerasimov |
| 2004/0220631 A1 | 11/2004 | Burnes et al. |
| 2004/0230233 A1 | 11/2004 | Gunderson et al. |
| 2004/0230242 A1 | 11/2004 | van Dam et al. |
| 2005/0124900 A1 | 6/2005 | Stadler et al. |
| 2005/0137636 A1 | 6/2005 | Gunderson et al. |
| 2005/0154421 A1 | 7/2005 | Ousdigian |
| 2005/0159785 A1 | 7/2005 | Rueter |
| 2006/0074454 A1 | 4/2006 | Freeberg |
| 2006/0116733 A1 | 6/2006 | Gunderson |
| 2006/0235476 A1 | 10/2006 | Gunderson et al. |
| 2008/0024293 A1 | 1/2008 | Stylos |
| 2008/0082012 A1 | 4/2008 | Gunderson et al. |
| 2008/0161872 A1 | 7/2008 | Gunderson |
| 2008/0215110 A1 * | 9/2008 | Gunderson ...................... 607/27 |
| 2010/0030292 A1 | 2/2010 | Sarkar et al. |
| 2010/0030293 A1 | 2/2010 | Sarkar et al. |
| 2010/0249627 A1 | 9/2010 | Zhang et al. |

OTHER PUBLICATIONS

Parsonnett et al, "Detection of Early Renal Transplant Rejection by Minimally-Invasive Monitoring of Impedance Variability", Mar. 30, 2007, vol. 22, No. 11, Barking, GB.

Valimaki et al., "Spectral analysis of cerebral electric impedance variability and arterial blood pressure variability in neonates with intraventricular haemorrhage", Cardiorespiratory Research Unit, University of Turku, Finland, and Biomedical Engineering Cen, Early Human Development, Shannon, IR, Aug. 1, 1988, p. 288, vol. 17, No. 1.

International Search Report, PCT/US2008/009027, Oct. 2, 2009, 7 Pages.

International Search Report and Written Opinion from Corresponding PCT Application Serial No. PCT/US2008/009027 dated Feb. 10, 2009 (17 pgs).

Response to Written Opinion for corresponding PCT Application Serial PCT/US2008/009027 filed Mar. 31, 2010 (19 pgs).

Examination Report for European application No. 08794736.2, dated Feb. 2, 2011, 5 pp.

Response to Examination Report dated Feb. 2, 2011, for European application No. 08794736.2, filed Jun. 6, 2011, 3 pp.

International Preliminary Report on Patentability for PCT Application No. PCT/US2008/009027, mail date Jul. 15, 2010, (16 pp).

EPO Communication from EP Application No. 08794736.2 dated Sep. 16, 2010 (2 pp.).

Office Action from U.S. Appl. No. 12/180,314, dated Mar. 23, 2012, 7 pp.

Response to Office Action dated Oct. 21, 2011, from U.S. Appl. No. 12/180,314, filed Jan. 23, 2012, 15 pp.

Response to Office Action dated Mar. 23, 2012, from U.S. Appl. No. 12/180,314, filed Jun. 20, 2012, 14 pp.

Office Action from U.S. Appl. No. 12/180,314, dated Oct. 21, 2011, 7 pp.

* cited by examiner

IMPEDANCE VARIABILITY ANALYSIS TO IDENTIFY LEAD-RELATED CONDITIONS

This application claims the benefit of U.S. Provisional Application No. 61/058,153, entitled "IMPEDANCE VARIABILITY ANALYSIS TO IDENTIFY LEAD-RELATED CONDITIONS" and filed on Jun. 2, 2008, the entire content of which is incorporated herein by reference.

TECHNICAL FIELD

This disclosure relates to implantable medical devices and associated devices, and, more particularly, to monitoring integrity of components associated with implantable medical devices.

BACKGROUND

A wide variety of implantable medical devices for delivering a therapy or monitoring a physiologic condition have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for sensing or delivery of stimulation. For example, electrodes or sensors may be carried at a distal portion of the lead. A proximal portion of the lead that may be coupled to an implantable medical device housing, which may contain electronic circuitry such as stimulation generation and/or sensing circuitry.

For example, implantable medical devices, such as cardiac pacemakers or implantable cardioverter defibrillators, provide therapeutic stimulation to the heart by delivering electrical therapy signals, such as pulses or shocks for pacing, cardioversion or defibrillation, via electrodes of one or more implantable leads. In some cases, such an implantable medical device may sense for intrinsic depolarizations of the heart, and control the delivery of such signals to the heart based on the sensing. When an abnormal rhythm is detected, which may be bradycardia, tachycardia or fibrillation, an appropriate electrical signal or signals may be delivered to restore the normal rhythm. For example, in some cases, an implantable medical device may deliver pacing, cardioversion or defibrillation signals to the heart of the patient upon detecting ventricular tachycardia, and deliver cardioversion or defibrillation electrical signals to a patient's heart upon detecting ventricular fibrillation. Pacing signals typically have a lower energy than the cardioversion or defibrillation signals.

Leads associated with such implantable medical devices typically include a lead body extending between a proximal lead end and a distal lead end and incorporate one or more exposed electrode or sensor elements located at or near the distal lead end. One or more elongated electrical conductors extend through the lead body from a connector assembly provided at a proximal lead end for connection with an associated implantable medical device to the one or more electrodes or sensor elements. Each electrical conductor is typically electrically isolated from any other electrical conductors and is encased within an outer sheath of the lead body that electrically insulates the lead conductors from body tissue and fluids.

Cardiac lead bodies tend to be continuously flexed by the beating of the heart. Other stresses may be applied to the lead body during implantation or lead repositioning. Patient movement can cause the route traversed by the lead body to be constricted or otherwise altered, causing stresses on the lead body. The electrical connection between implantable medical device connector elements and the lead connector elements can be intermittently or continuously altered. In some cases, changes in leads or connections may result in intermittent or continuous changes in lead impedance.

Short circuits, open circuits or significant changes in impedance may be referred to, in general, as lead-related conditions. In the case of cardiac leads, sensing of an intrinsic heart rhythm through a lead can be altered by lead-related conditions. Structural modifications to leads, conductors or electrodes may alter sensing integrity. Furthermore, impedance changes in the stimulation path due to lead-related conditions may affect sensing and stimulation integrity for pacing, cardioversion, or defibrillation. In addition to lead-related conditions, conditions associated with sensor devices or sensing circuitry may affect sensing integrity.

SUMMARY

In general, the disclosure relates to lead monitoring techniques for detecting or predicting a possible condition in an implantable medical electrode lead or in a device-lead pathway or connection. The techniques may involve calculating mean impedance values and impedance variability values for an electrical path associated with the lead to predict or detect a possible condition with the lead. Using these techniques, subtle changes in impedance that may precede subsequent conditions with the lead may be detected. Given a time series of impedance measurements collected at regular intervals, these techniques may allow adaptation of lead monitoring to expected impedance values for a patient and/or expected variability of impedances over time for the patient. Subsequent measurements of impedance that are statistical outliers relative to historical values may represent evidence of potential conditions with the lead.

In one example, a method comprises determining an impedance value for an electrical path based on a plurality of measured impedance values for the electrical path, wherein the electrical path comprises a plurality of electrodes for at least one of stimulation or sensing, and determining an impedance variability value based on at least one of the plurality of measured impedance values. The method further comprises determining a threshold value based on the determined impedance value and the impedance variability value, comparing a newly measured impedance value for the electrical path to the threshold value to determine if there is a possible condition with the electrical path, and indicating a possible condition based on the comparison.

In one example, an implantable medical device comprises a module configured to measure impedance values for an electrical path associated with at least one of implantable lead and a processor, wherein the electrical path comprises a plurality of electrodes for at least one of patient stimulation or sensing. The processor may be configured to determine an impedance value for the electrical path based on a plurality of measured impedance values for the electrical path, determine an impedance variability value based on at least one of the plurality of measured impedance values, determine a threshold value based on the determined impedance value and the impedance variability value, compare a newly measured impedance value for the electrical path to the threshold value, and indicate a possible condition of the electrical path based on the comparison.

In one example, a system comprises a module configured to receive impedance measurement values for an electrical path associated with at least one lead and a processor, wherein the electrical path comprises a plurality of electrodes for at least one of patient stimulation or sensing. The processor is configured to determine an impedance value for the electrical path based on a plurality of measured impedance values for the electrical path, determine an impedance variability value based on at least one of the plurality of measured impedance values, determine a threshold value based on the determined impedance value and the impedance variability value, compare a newly measured impedance value for the electrical path to the threshold value, and indicate a possible condition of the electrical path based on the comparison.

In one example, a system comprises an impedance measurement module configured to receive impedance measurement values for an electrical path associated with at least one medical lead wherein the electrical path comprises a plurality of electrodes for at least one of patient stimulation or sensing, and also a threshold update module. The threshold update module is configured to determine an impedance value for the electrical path based on a plurality of measured impedance values for the electrical path, to determine an impedance variability value based on at least one of the plurality of measured impedance values, and to determine a threshold value based on the determined impedance value and the impedance variability value. The system further comprises a threshold comparison module configured to compare a newly measured impedance value for the electrical path to the threshold value, and an integrity indication module configured to indicate a possible condition of the electrical path based on the comparison.

In one example, a computer-readable medium comprising instructions for causing one or more processors to determine an impedance value for an electrical path based on a plurality of measured impedance values for the electrical path, wherein the electrical path comprises a plurality of electrodes for at least one of stimulation or sensing, determine an impedance variability value based on at least one of the plurality of measured impedance values, determine a threshold value based on the determined impedance value and the impedance variability value, compare a newly measured impedance value for the electrical path to the threshold value, and indicate a possible condition of the electrical path based on the comparison.

The details of one or more examples of techniques based on the disclosure are set forth in the accompanying drawings and the description below. Other features, objects, and advantages of the disclosure will be apparent from the description and drawings, and from the claims.

DETAILED DESCRIPTION

Figure 1:
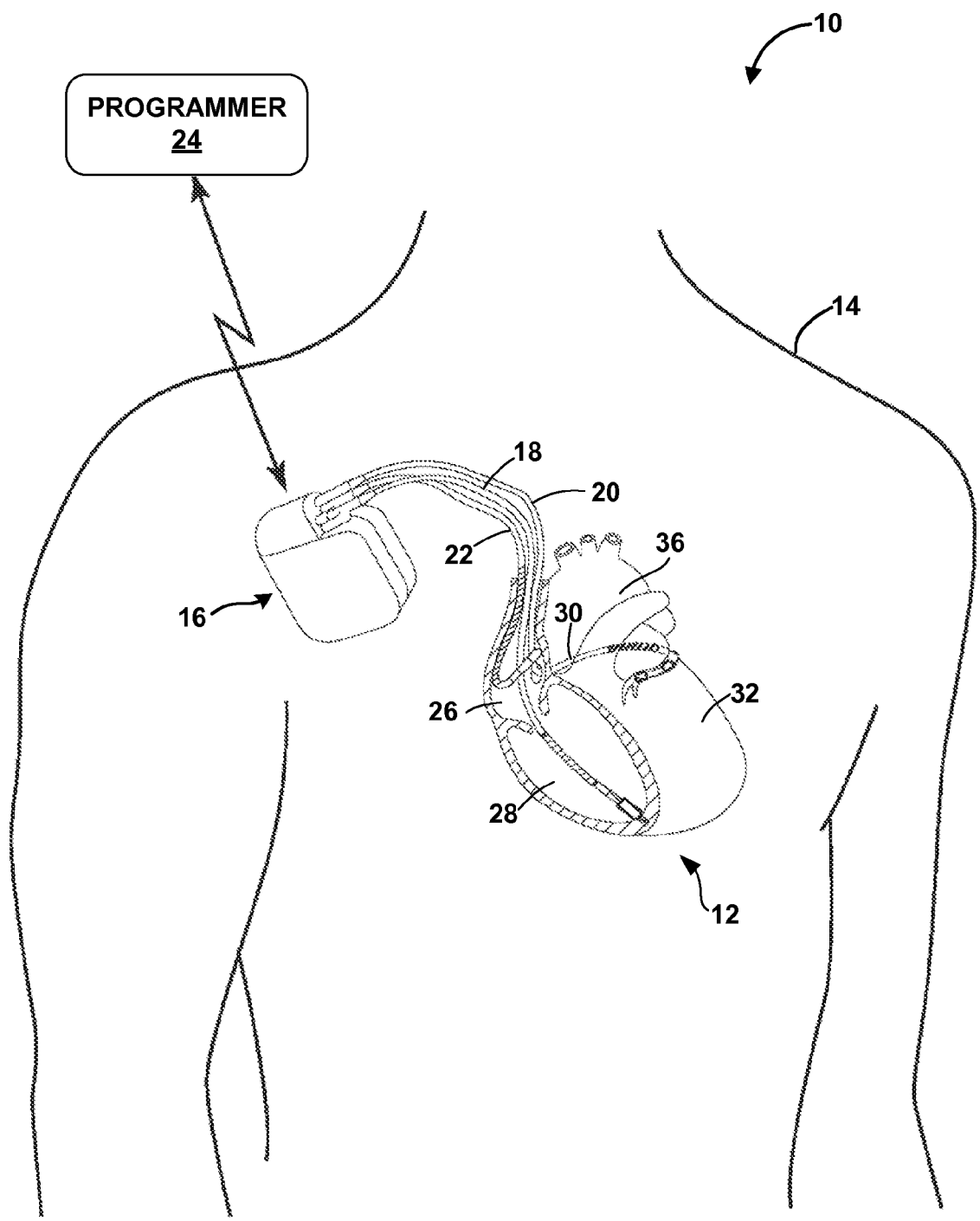
FIG. 1 is a conceptual diagram illustrating an example therapy system that may be used to provide therapy to a heart of a patient.

FIG. 1 is a conceptual diagram illustrating an example therapy system 10 that may be used to provide therapy to heart 12 of patient 14. Patient 12 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provides electrical therapy signals to heart 12 via electrodes coupled to one or more of leads 18, 20, and 22. IMD 16 may, as described in greater detail below, collect and measure impedance values associated with one or more of leads 18, 20, and 22. IMD 16 and/or programmer 24 may analyze the measured impedance values for any given lead, and may compare these values, or other computed values, to determined thresholds and identify any possible conditions with the lead. For example, IMD 16 and/or programmer 24 may, as a result of one or more comparisons, determine that one or more of leads 18, 20, and 22 has a lead-related condition.

Various example techniques, and associated devices and systems, for monitoring lead integrity are described herein. Although many of the techniques that are described relate to cardiac therapy, these and other techniques could be applied to other therapies in which lead integrity may be important or relevant, such as, for example, spinal cord stimulation, deep brain stimulation, pelvic floor stimulation, gastric stimulation, occipital stimulation, or functional electrical stimulation. These and other techniques could also be applied to monitoring technologies in which no therapy is delivered to patient 14.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, and 22, or a power source of IMD 16.

The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

In one embodiment, IMD 16 is capable of collecting impedance measurement data for one or more of electrode leads 18, 20, and 22. Upon collection of such measurement data, IMD 16 and/or programmer 24 are capable, either independently or in combination, of calculating mean impedance values and impedance variability values for an electrode lead to predict or detect a possible lead-related condition. Given a time series of impedance measurements collected at regular intervals by IMD 16, IMD 16 and/or programmer 24 can make calculations that allow adaptation to expected values and/or expected variability of impedances over time for a given patient, such as patient 14, in a manner similar to the methods of statistical process control. Subsequent measurements of impedance that are statistical outliers relative to historical values then may represent evidence of potential conditions with the electrode lead. IMD 16 and/or programmer 24 are capable of generating alerts to indicate any potential conditions with the lead.

Figure 2:
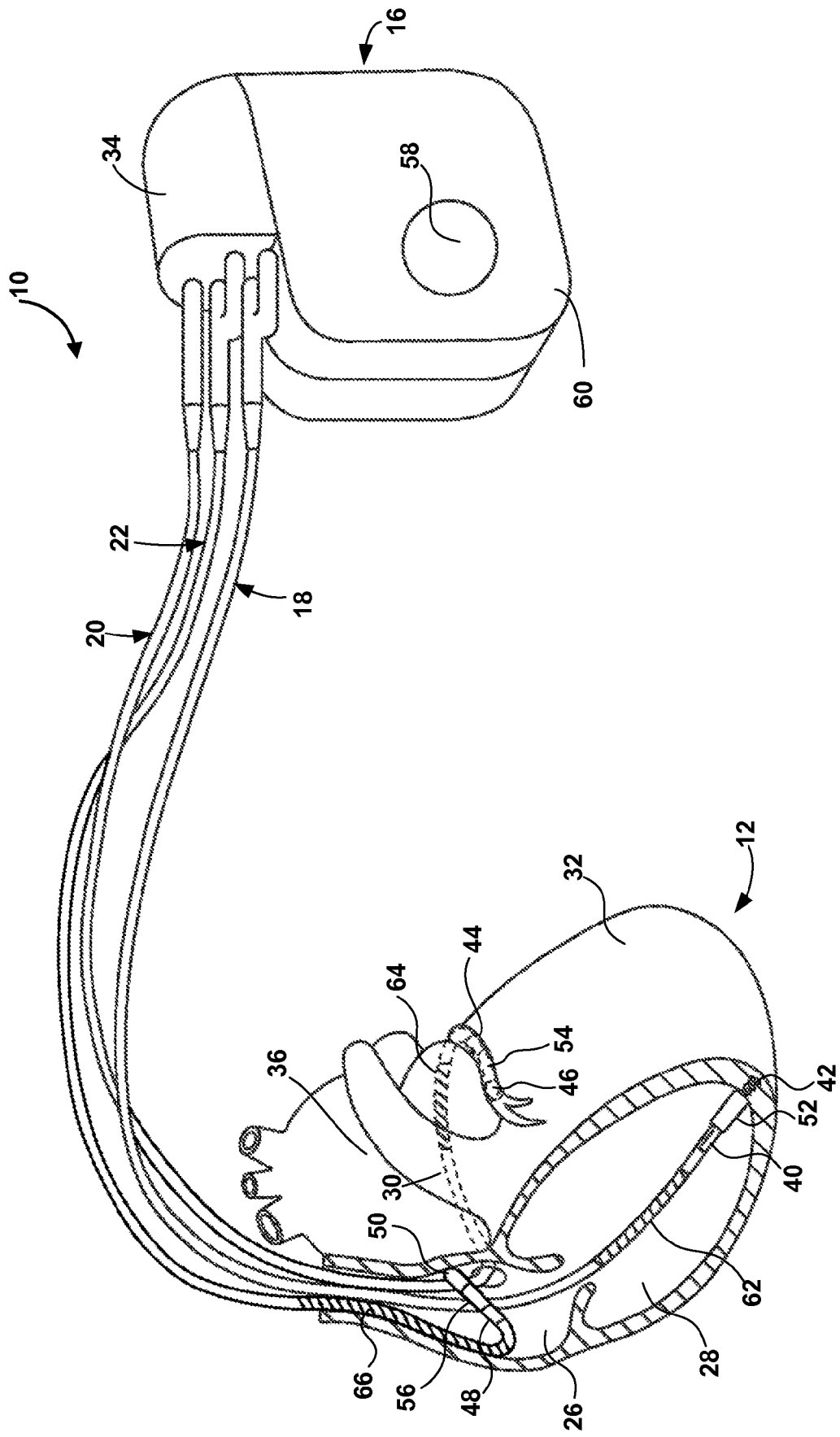
FIG. 2 is a conceptual diagram illustrating the implantable medical device (IMD) and the leads of the therapy system shown in FIG. 1 in greater detail, based on one example.

FIG. 2 is a conceptual diagram illustrating IMD 16 and leads 18, 20, and 22 of therapy system 10 in greater detail. Leads 18, 20, 22 may be electrically coupled to a stimulation generator and a sensing module of IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins, or another suitable mechanical coupling mechanism.

Each of the leads 18, 20, 22 includes an elongated insulative lead body, which may carry a number of concentric coiled conductors separated from one another by tubular insulative sheaths. In some cases, each of the leads 18, 20, 22 may include cable conductors. Bipolar electrodes 40 and 42 are located adjacent to a distal end of lead 18. In addition, bipolar electrodes 44 and 46 are located adjacent to a distal end of lead 20 and bipolar electrodes 48 and 50 are located adjacent to a distal end of lead 22. Electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As described in further detail with reference to FIG. 4, housing 60 may enclose a stimulation generator that generates cardiac pacing pulses and defibrillation shocks, as well as a sensing module for monitoring the patient's heart rhythm.

Leads 18, 20, 22 also include elongated electrodes 62, 64, 66, respectively, which may take the form of a coil. IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Elongated electrodes 62, 64 and 66 may also be used to sense electrical activity of heart 12. For example, a bipolar electrode combination may include elongate electrode 62 and electrode 42. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples therapy systems may include three transvenous leads located as illustrated in FIGS. 1 and 2, and an additional lead located within or proximate to left atrium 36. As other examples, a therapy system may include a single lead that extends from IMD 16 into right atrium 26 or right ventricle 28, or two leads that extend into a respective one of the right ventricle 28 and right atrium 26. An example of this type of therapy system is shown in FIG. 3.

Figure 3:
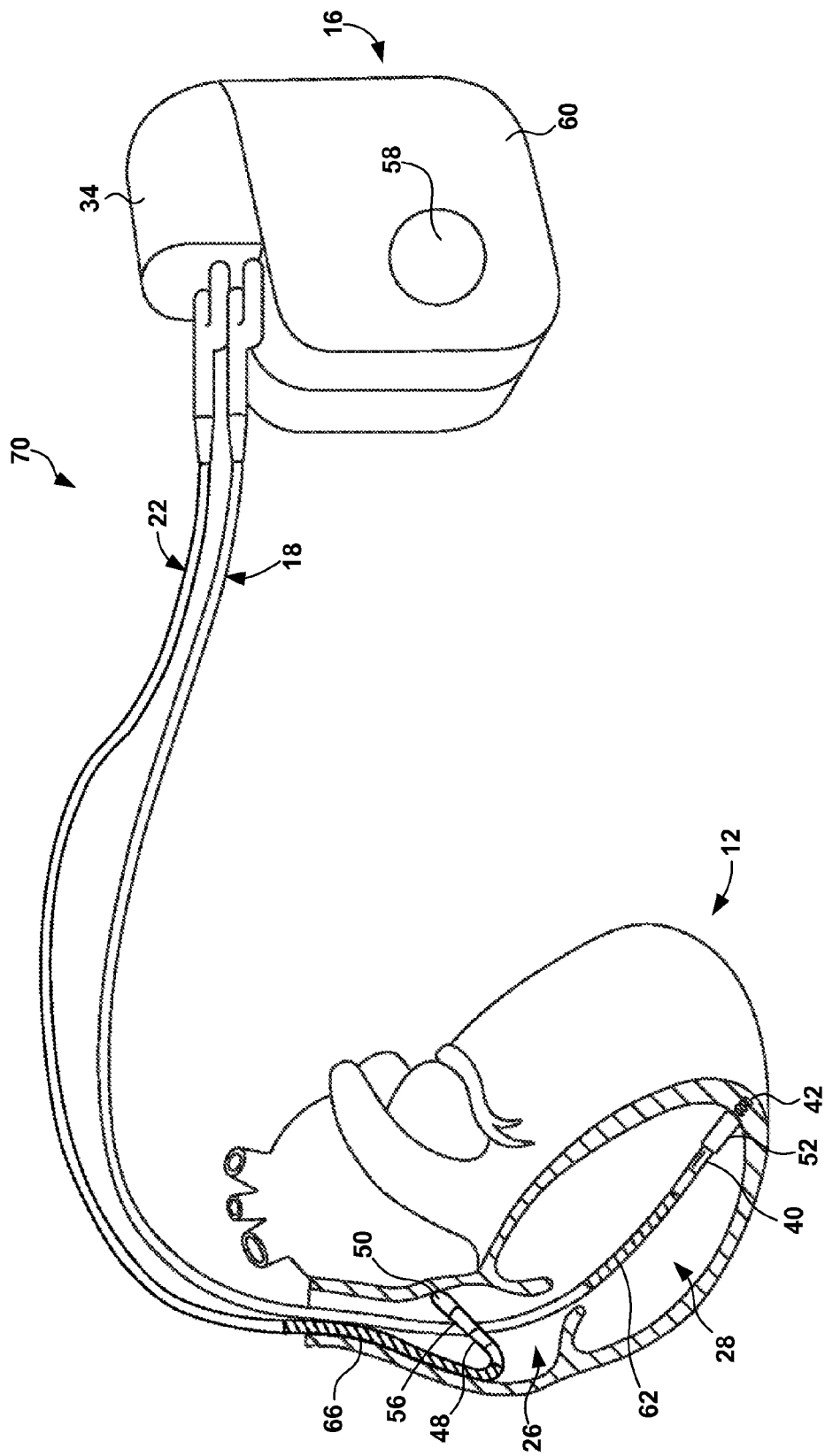
FIG. 3 is a conceptual diagram illustrating another example of a therapy system, which is similar to the therapy system shown in FIGS. 1-2, but which includes two leads rather than three leads.

FIG. 3 is a conceptual diagram illustrating another example therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12.

Figure 4:
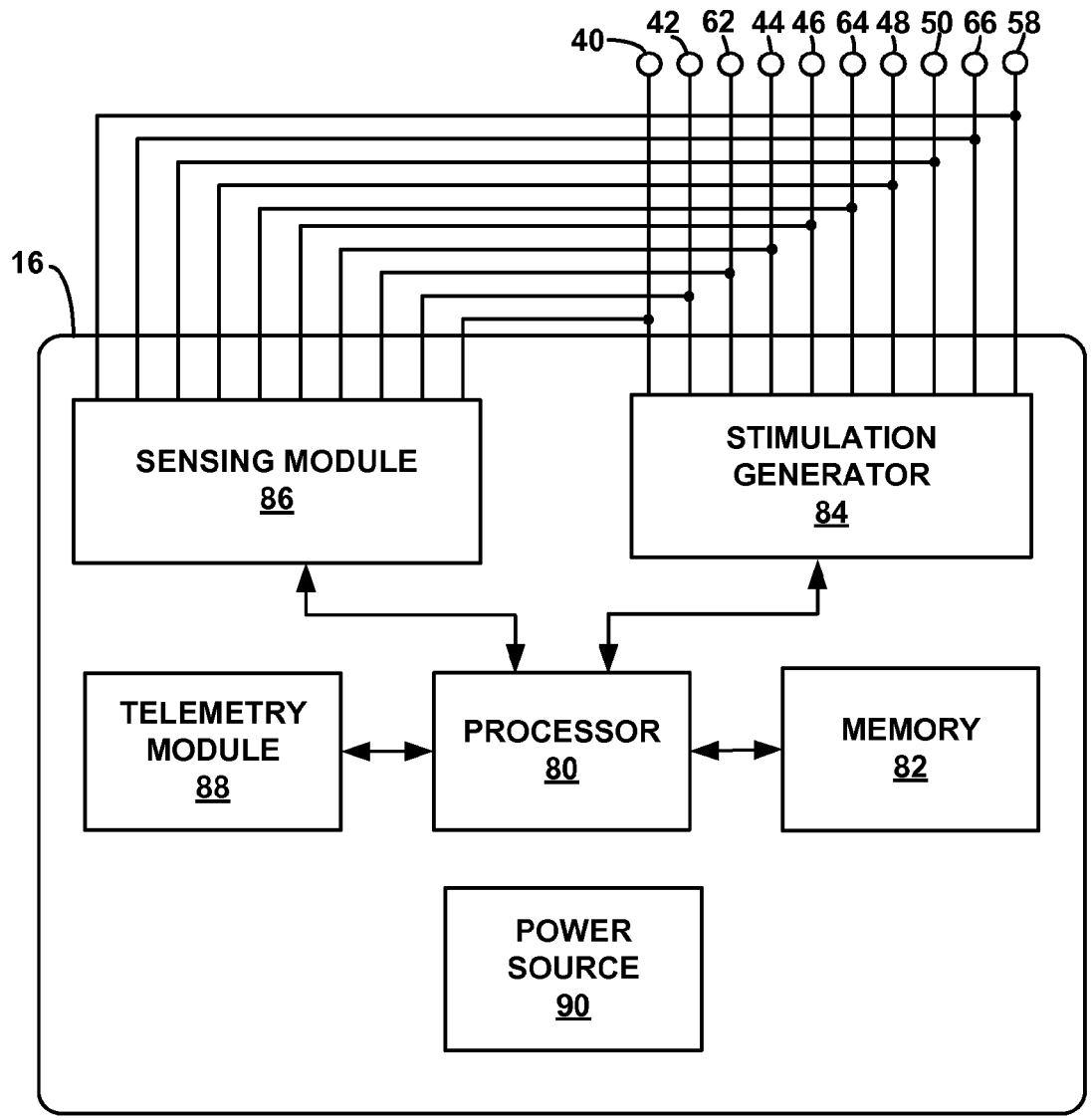
FIG. 4 is a functional block diagram illustrating an example configuration of the IMD shown in FIG. 1.

FIG. 4 is a functional block diagram of one example of IMD 16, which includes processor 80, memory 82, stimulation generator 84, sensing module 86, telemetry module 88, and power source 90. Processor 80 may comprise one or more processors. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 based on a selected one or more of therapy programs, which may be stored in memory 82. Specifically, processor 44 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. A switch matrix may also be provided to connect stimulation generator 84 to one or more of electrodes 40, 42, 44, 46, 48, 50, 58, 62, 64, and 66. Stimulation generator 84 is configured to generate and deliver electrical stimulation therapy to heart 12. For example, stimulation generator 84 may deliver defibrillation shocks to heart 12 via at least two electrodes 58, 62, 64, 66. Stimulation generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, stimulation generator 84 delivers pacing, cardioversion, or defibrillation stimulation in the form of electrical pulses. In other examples, stimulation generator may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12, e.g., via electrocardiogram (ECG) signals. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprise an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 84 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, 36, or 32 of heart 12.

In some examples, sensing module 84 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the patient's heart rhythm by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves. Stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect an arrhythmia event, such as ventricular fibrillation or ventricular tachycardia.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. are incorporated herein by reference in their entireties. However, other arrhythmia detection methodologies may also be employed by processor 80 in other examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by stimulation generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation pulses to heart 12, stimulation generator 84 may include a high voltage charge circuit and a high voltage output circuit. If IMD 16 is configured to generate and deliver pacing pulses to heart 12, stimulation generator 84 may include a low voltage charge circuit and a low voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor may be monitored, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 84 is controlled by the cardioversion/defibrillation control module of processor 80. Following delivery of the fibrillation or tachycardia therapy, processor 80 may return stimulation generator 84 to a cardiac pacing function and await the next successive interrupt due to pacing or the occurrence of a sensed atrial or ventricular depolarization.

Stimulation generator 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching module of stimulation generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

In one embodiment, sensing module 86 and/or processor 80 are capable of collecting, measuring, and/or calculating impedance data for each of leads 18, 20, and 22. In this embodiment, sensing module 86 and/or processor 80 measure impedance values during delivery of an electrical signal between at least two electrodes that are coupled to one or more of leads 18, 20 and 22. Processor 80 may control signal generator 84 to deliver the electrical signal between the electrodes. For example, sensing module 86 and/or processor 80 may collect, measure, and/or calculate impedance data for lead 18 based on delivery of an electrical signal between electrodes 40 and 42, impedance data for lead 20 based on delivery of an electrical signal between electrodes 44 and 46, and impedance data for lead 22 based on delivery of an electrical signal between electrodes 48 and 50. Sensing module 86 and/or processor 80 may collect, measure, and/or calculate impedance values for any of a variety of electrical paths that include one or more electrodes on one or more of leads 18, 20, and 22 based on delivery of a signal between any combination of two or more of electrodes 40, 42, 44, 46 and 48, elongated electrodes 62, 64 and 66, and housing electrode 58. IMD 16 may store measured impedance values in memory 82.

In some examples, IMD 16 may perform an impedance measurement by delivering, from stimulation generator 84, a voltage pulse between first and second electrodes, and measuring a resulting current. IMD 16, e.g., processor 80, may calculate a resistance based upon the voltage amplitude of the pulse and the measured amplitude of the resulting current. In these examples, stimulation generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12.

In some examples, IMD 16 may be entirely dedicated to monitoring and/or impedance measurements, i.e., the techniques described herein are not limited to implantation in devices that deliver stimulation or any other type of therapy. In these examples, stimulation generator 84 may be configured to deliver signals that do not deliver stimulation therapy to heart 12.

In certain cases, IMD 16 may perform impedance measurement by delivering, from stimulation generator 84, a current pulse across first and second electrodes, and measuring a resulting voltage. IMD 16 may calculate a resistance based upon the current amplitude of the pulse and the measured amplitude of the resulting voltage. Sensing module 86 may include circuitry for measuring amplitudes of resulting currents or voltages, such as sample and hold circuitry. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, IMD 16 may collect impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components. Impedance data may include actual, measured impedance values, or may include values that can be used to calculate impedance (such as current and/or voltage values).

In one embodiment, IMD 16 may analyze the measured impedance values, and may compare these values, or other computed values, to determined thresholds and identify any possible conditions with one or more of leads 18, 20 and 22. For example, IMD 16 may, as a result of one or more comparisons, determine that one or more of leads 18, 20, and 22 has a lead-related condition. IMD 16 may send impedance measurement and/or analysis data to programmer 24 via telemetry module 88.

Figure 5:
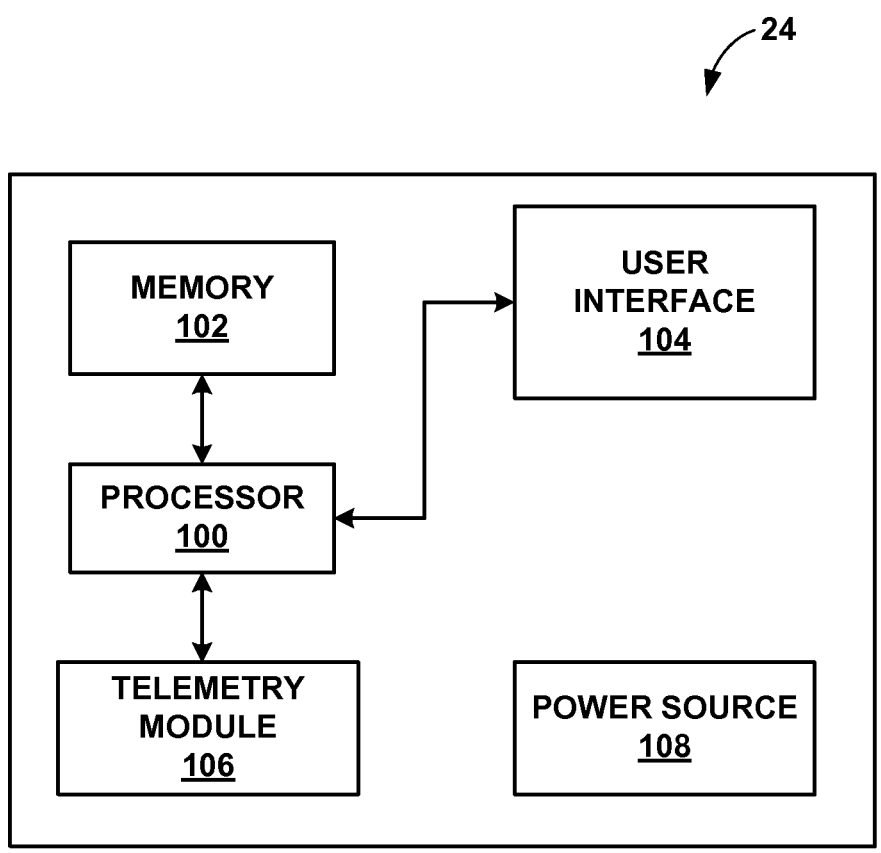
FIG. 5 is a functional block diagram illustrating an example configuration of the programmer shown in FIG. 1.

FIG. 5 is block diagram of an example programmer 24. As shown in FIG. 5, programmer 24 includes processor 100, memory 102, user interface 104, telemetry module 106, and power source 108. Processor 100 may comprise one or more processors. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 102 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 102, which may be coupled to an internal antenna or an external antenna. An external antenna that is coupled to programmer 24 may correspond to the programming head that may be placed over heart 12, as described above with reference to FIG. 1. Telemetry module 102 may be similar to telemetry module 88 of IMD 16 (FIG. 4).

Telemetry module 102 may also be configured to communicate with another computing device via wireless communication techniques, or direct communication through a wired connection. Examples of local wireless communication techniques that may be employed to facilitate communication between programmer 24 and another computing device include RF communication based on the 802.11 or Bluetooth specification sets, infrared communication, e.g., based on the IrDA standard, or other standard or proprietary telemetry protocols. In this manner, other external devices may be capable of communicating with programmer 24 without needing to establish a secure wireless connection.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 104 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

In one embodiment, programmer 24 may receive impedance measurement and/or data that may be used to calculate impedance, such as measured voltage or current values, from IMD 16 via telemetry module 106. As described previously, IMD 16 may collect impedance measurement data for one or more of leads 18, 20, and 22. In some cases, IMD 16 may periodically collect impedance measurement data, such an on a regular basis (e.g., every hour, day, week, etc.). In some cases, IMD 16 may non-periodically collect impedance measurement data. For example, the collection of impedance measurement data may be triggered by a particular type of event, such as the occurrence of a short interval or short interval count.

IMD 16 and/or programmer 24 may analyze the measured impedance values for any given lead, and may compare these values, or other computed values, to determined thresholds and identify any possible conditions with the lead. For example, IMD 16 may, in some cases, provide impedance measurement data to programmer 24. Programmer 24 may then analyze the measurement data to determine that one or more of leads 18, 20, and 22 has a lead-related condition.

Figure 6:
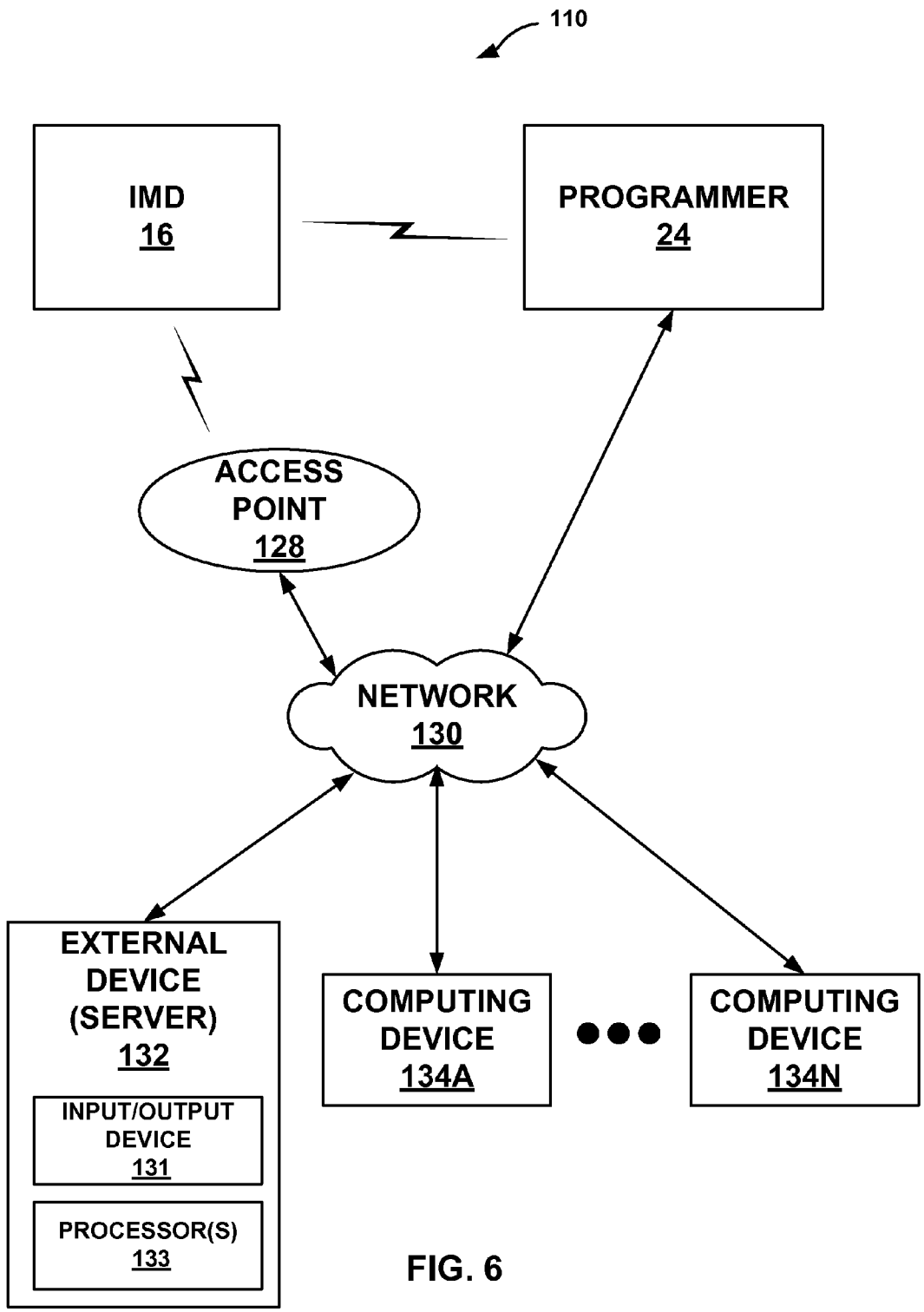
FIG. 6 is a block diagram illustrating an example system that includes an external device, such as a server, and one or more computing devices that are coupled to the IMD and programmer shown in FIG. 1 via a network.

FIG. 6 is a block diagram illustrating a system 110 that includes an external device 132, such as a server, and one or more computing devices 134A-134N that are coupled to IMD 16 and programmer 24 shown in FIG. 1 via a network 130, based on one embodiment. In this embodiment, IMD 16 uses its telemetry module 88 to communicate with programmer 24 via a first wireless connection, and to communication with an access point 128 via a second wireless connection. In some cases, IMD 16 may communicate with other access points, programmers, and/or computing devices (not shown) that are co-located with patient 14 via one or more wireless connections.

In the example of FIG. 6, access point 128, programmer 24, external device 132, and computing devices 134A-134N are interconnected, and able to communicate with each other, through network 130. In some cases, one or more of access point 128, programmer 24, external device 132, and computing devices 134A-134N may be coupled to network 130 through one or more wireless connections. IMD 16, programmer 24, external device 132, and computing devices 134A-134N may each comprise one or more processors, such as one or more microprocessors, DSPs, ASICs, FPGAs, programmable logic circuitry, or the like, that may perform various functions and operations, such as those described herein. In some embodiments, additional access points, programmers, and/or computing devices that are coupled to IMD 16 and co-located with patient 14 (not shown) may also each comprise one or more processors, such as one or more microprocessors, DSPs, ASICs, FPGAs, programmable logic circuitry, or the like, that may perform various functions and operations, such as those described herein.

Access point 128 may comprise a device that connects to network 130 via any of a variety of connections, such as telephone dial-up, digital subscriber line (DSL), or cable modem connections. In other embodiments, access point 128 may be coupled to network 130 through different forms of connections, including wired or wireless connections. In some embodiments, access point 128 may be co-located with patient 14 and may comprise one or more programming units and/or computing devices (e.g., one or more monitoring units) that may perform various functions and operations described herein. For example, access point 128 may include a home-monitoring unit that is co-located with patient 14 and that may monitor the activity of IMD 16.

During operation, IMD 16 may collect, measure, and store various forms of diagnostic data. For example, as described previously, IMD 16 may collect impedance measurement data for one or more of leads 18, 20, and 22. In certain cases, IMD 16 may directly analyze collected diagnostic data and generate any corresponding reports or alerts. In some cases, however, IMD 16 may send diagnostic data to programmer 24 and/or external device 132, either wirelessly or via access point 128 and network 130, for remote processing and analysis.

For example, IMD 16 may send programmer 24 collected impedance measurement data, which is then analyzed by programmer 24. Programmer 24 may generate reports or alerts after analyzing the impedance data and determining that there may be a possible condition with one or more of leads 18, 20, and 22.

In some cases, IMD 16 and/or programmer 24 may combine all of the diagnostic data into a single displayable lead integrity report, which may be displayed on programmer 24. The lead integrity report contains diagnostic information concerning one or more electrode leads that are coupled to IMD 16, such as leads 18, 20, or 22. A clinician or other trained professional may review and/or annotate the lead integrity report, and possibly identify any lead-related conditions.

In another example, IMD 16 may provide external device 132 with collected diagnostic data via access point 128 and network 130. External device 132 includes one or more processors 133. In some cases, external device 132 may request such data, and in some cases, IMD 16 may automatically or periodically provide such data to external device 132. Upon receipt of the diagnostic data via input/output device 131, external device 132 is capable of analyzing the data and generating reports or alerts upon determination that there may be a possible condition with one or more of leads 18, 20, and 22.

In one embodiment, external device 132 may combine the diagnostic data into a lead integrity report. One or more of computing devices 134A-134N may access the report through network 130 and display the report to users of computing devices 134A-134N. In some cases, external device 132 may automatically send the report via input/output device 131 to one or more of computing devices 134A-134N as an alert, such as an audio or visual alert. In some cases, external device 132 may send the report to another device, such as programmer 24, either automatically or upon request. In some cases, external device 132 may display the report to a user via input/output device 131.

In one embodiment, external device 132 may comprise a secure storage site for diagnostic information that has been collected from IMD 16 and/or programmer 24. In this embodiment, network 130 may comprise an Internet network, and trained professionals, such as clinicians, may use computing devices 134A-134N to securely access stored diagnostic data on external device 132. For example, the trained professionals may need to enter usernames and passwords to access the stored information on external device 132. In one embodiment, external device 132 may be a CareLink server provided by Medtronic, Inc., of Minneapolis, Minn.

Figure 7:
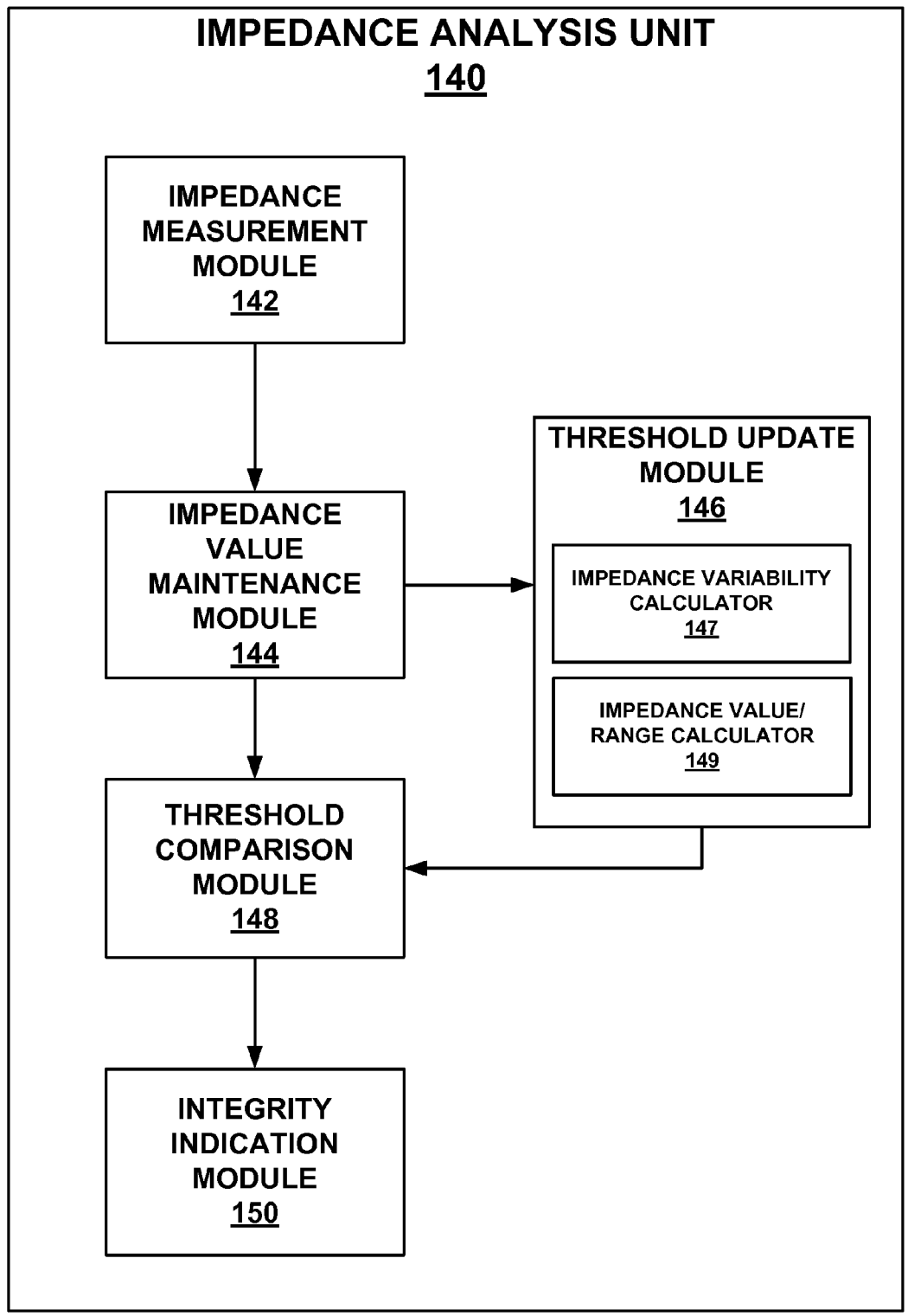
FIG. 7 is a functional block diagram illustrating multiple modules of an impedance analysis unit, based on one example.

FIG. 7 is a block diagram illustrating multiple modules of an example impedance analysis unit 140. Each module 142, 144, 146, 148, and 150 of impedance analysis unit 140 may be implemented in one or more processors, such as processor 80 of IMD 16, processor 100 of programmer 24, and/or processor(s) 133 of external device 132 to provide the functionality of impedance analysis unit 140. The modules of impedance analysis unit 140 may be embodied as one or more hardware modules, software modules, firmware modules, or any combination thereof. Impedance analysis unit 140 may analyze impedance measurement data, such as on a periodic basis, and compare such data with calculated threshold values to identify possible lead-related conditions.

As shown in FIG. 7, impedance analysis unit 140 includes an impedance measurement module 142, an impedance value maintenance module 144, a threshold update module 146, a threshold comparison module 148, and an integrity indication module 150. Impedance measurement module 142 may measure impedance values for one or more electrical paths provided by one or more electrode leads. For example, impedance measurement module 142 may measure impedance values on a periodic basis, such as on an hourly basis, daily basis, weekly basis, or the like. In some cases, impedance measurement module 142 may measure impedance values every portion of an hour (e.g., every minute).

Based on the measured impedance values, impedance value maintenance module 144 may determine maximum and/or minimum impedance values for each of one or more electrical paths during a given period of time. For example, if impedance values are measured for an electrical path multiple times in a given week, impedance value maintenance module 144 is able to determine a maximum and minimum impedance value for that week. Impedance value maintenance module 144 may also determine an impedance range value for the week, which may be the difference between the determined maximum and minimum values for that week (difference range). (As used herein, the term "difference" may indicate either a signed or an absolute (unsigned) difference value.)

In certain cases, impedance value maintenance module 144 may maintain various running, updated impedance values during a given period of time. For example, if impedance measurement module 142 provides impedance measurements on a daily basis, impedance value maintenance module 144 may maintain a maximum impedance value, a minimum impedance value, and a range impedance value for a given week, where each of these values may be updated daily based on newly measured impedance values received from impedance measurement module 142. Thus, if the daily measured impedance value exceeds the current maximum impedance value for the week, the maximum impedance value may be set equal to the daily measured value. Similarly, if the daily measured impedance value falls below the current minimum impedance value for the week, the minimum impedance value may be set equal to the daily measured value. The range impedance value may be similarly updated, as appropriate. At the end of the week, impedance value maintenance module 144 has stored a maximum impedance value, a minimum impedance value, and a range impedance value for that week.

Threshold update module 146 is capable of maintaining and updating one or more threshold values that may be used by threshold comparison module 148. In some cases, these threshold values may be based upon impedance variability values (provided by impedance variability calculator 147) and/or values of impedance and/or range provided by value/range calculator 149.

Impedance value/range calculator 149 is capable of periodically computing values of impedance and/or range values using the determined values that are provided by impedance value maintenance module 144. In some cases, impedance value/range calculator 149 is capable of computing mean values of impedance and/or range values. For example, if impedance value maintenance module 144 updates impedance data, such as maximum and/or minimum impedance values, on a daily basis, impedance value/range calculator 149 may calculate an updated mean maximum impedance value each week based upon the maximum impedance value for the current week and previous weeks, and may calculate an updated, mean minimum impedance value each week based upon the minimum impedance value for the current week and previous weeks. In some cases, impedance value/range calculator 149 is capable of computing values of impedance and/or range values based upon any form of central tendency, such as a mean, median, or mode.

In addition, impedance value/range calculator 149 is also capable of periodically calculating an impedance range value based on difference ranges between maximum and minimum impedance values. For example, an updated impedance range value may be calculated each week based upon both the maximum and minimum impedance values for the current week and previous weeks.

Impedance variability calculator 147 may calculate impedance variability values based on at least one of the impedance values provided by impedance value maintenance module 144. For example, in some cases, impedance variability calculator 147 may calculate impedance variability values based on differences between determined impedance values and impedance values provided by impedance value maintenance module 144. (As used herein, the term "difference" may indicate either a signed or an absolute (unsigned) difference value.) For example, impedance variability calculator 147 may calculate an updated, weekly maximum impedance variability value based on a difference between a determined maximum impedance value (calculated by calculator 149) and a maximum impedance value (such as a weekly maximum impedance value) that is provided by impedance value maintenance module 144 at a particular point in time, such as at the end of a given week.

Impedance variability calculator 147 may calculate an updated, weekly impedance variability value based on a difference between a determined minimum impedance value (calculated by calculator 149) and a minimum impedance value (such as a weekly minimum impedance value) that is provided by impedance value maintenance module 144. Impedance variability calculator 147 may also calculate an updated, weekly impedance range variability value based on a difference between a determined impedance range value (calculated by calculator 149) and a range impedance value (such as, for example, a weekly impedance range value, or difference range, based on the difference between a weekly maximum value and a weekly minimum value) provided by impedance value maintenance module 144.

Threshold update module 146 may determine a maximum threshold value based on a determined maximum impedance value provided by impedance value/range calculator 149 and an impedance variability value provided by impedance variability calculator 147. Threshold update module 146 may also determine a minimum threshold value based on a determined minimum impedance value provided by impedance value/range calculator 149 and an impedance variability value provided by impedance variability calculator 147. In some cases, threshold update module 146 may determine a threshold range value based on a determined impedance range value provided by impedance value/range calculator 149 and an impedance range variability value provided by impedance variability calculator 147.

Threshold comparison module 148 may receive one or more threshold values from threshold update module 146. Threshold comparison module 148 may compare one or more current impedance values from impedance value maintenance module 144 to these thresholds to indicate, or determine, if there may be a possible condition of the electrode lead, e.g., of an electrical path including at least one electrode of the lead. For example, threshold comparison module 148 may obtain a threshold value from threshold update module 146, which may be based on a mean impedance value provided by impedance value/range calculator 149 and an impedance variability value provided by impedance variability calculator 147. Threshold comparison module 148 may then compare a newly measured value provided by impedance value maintenance module 144 (provided by impedance measurement module 142) to this threshold. Threshold update module 146 may update various threshold values on a periodic (e.g., weekly) basis, but may provide the most current threshold values at any given time to threshold comparison module 148.

For example, threshold comparison module 148 may obtain a maximum threshold value from threshold update module 146 that is based on a determined maximum impedance value provided by impedance value/range calculator 149 and an impedance variability value provided by impedance variability calculator 147. Threshold comparison module 148 may then compare a newly measured maximum value provided by impedance value maintenance module 144 to this maximum threshold value, to see if the maximum value exceeds the threshold. Threshold comparison module 148 may also obtain a minimum threshold value from threshold update module 146 and then compare a newly measured minimum value to this minimum threshold value, to see if the minimum value falls below the threshold.

In some cases, threshold comparison module 148 may obtain a threshold range value from threshold update module 146. Threshold comparison module 148 may then compare a newly measured range value (maximum minus minimum) provided by impedance value maintenance module 144 to this threshold value, to see if the range value exceeds the threshold.

Integrity indication module 150 is capable of providing an indication for one or more leads or electrical paths of leads based upon the results provided by threshold comparison module. If there are no suspected lead-related conditions, integrity indication module 150 may provide no indication, or may provide an indication that a given lead is in working, or operational, condition. If, however, the results of threshold comparison module 148 indicate a possible condition, integrity indication module 150 may indicate this possible condition of an electrode lead or electrical path, such as, for example, by providing a visual and/or audible alert (or alarm).

In certain cases, integrity indication module 150 may provide alarms or notifications via wireless communication. For example, if integrity indication module 150 is implemented by IMD 16, it may send an alarm or notification wirelessly to programmer 24 and/or to network 130 (in which case it may be sent to external device 132 and/or devices 134A-134N shown in FIG. 6). In this fashion, doctors, nurses, review centers, and the like, may obtain wireless notification of a condition or an alarm. In some cases, the notification may comprise a visual and/or audible alert, or may even comprise a vibration (such as on a paging device).

In some cases, alarm conditions could cause IMD 16 to alert patient 14. For example, if an alarm condition exists, IMD 16 may initiate stimulation of local muscles of patient 14 to provide an indication of such condition. IMD 16 may also provide wireless communication of such alarm condition to an external device near to or worn by patient 14. Additionally, any alarm conditions could potentially change the behavior of IMD 16, such as, for example, altering detection of arrhythmias and/or therapy delivery means.

For example, if threshold comparison module 148 provides a result indicating that a maximum impedance value exceeds a determined maximum threshold, or that a minimum impedance value falls below a determined minimum threshold, integrity indication module 150 may indicate a possible condition for the lead. If threshold comparison module 148 provides a result indicating that a range value exceeds a determined range threshold, integrity indication module 150 may also provide such an indication.

The functionality of modules 142, 144, 146, 148, and 150 may be provided for multiple electrical paths. These multiple electrical paths may be associated with one or more leads, such as leads 18, 20, and/or 22. Each electrical path may comprise multiple electrodes for the one or more leads. By using modules 142, 144, 146, 148, and 150 to test multiple electrical paths, impedance analysis unit 140 is capable of analyzing one or more leads for possible lead-related conditions.

Figure 8:
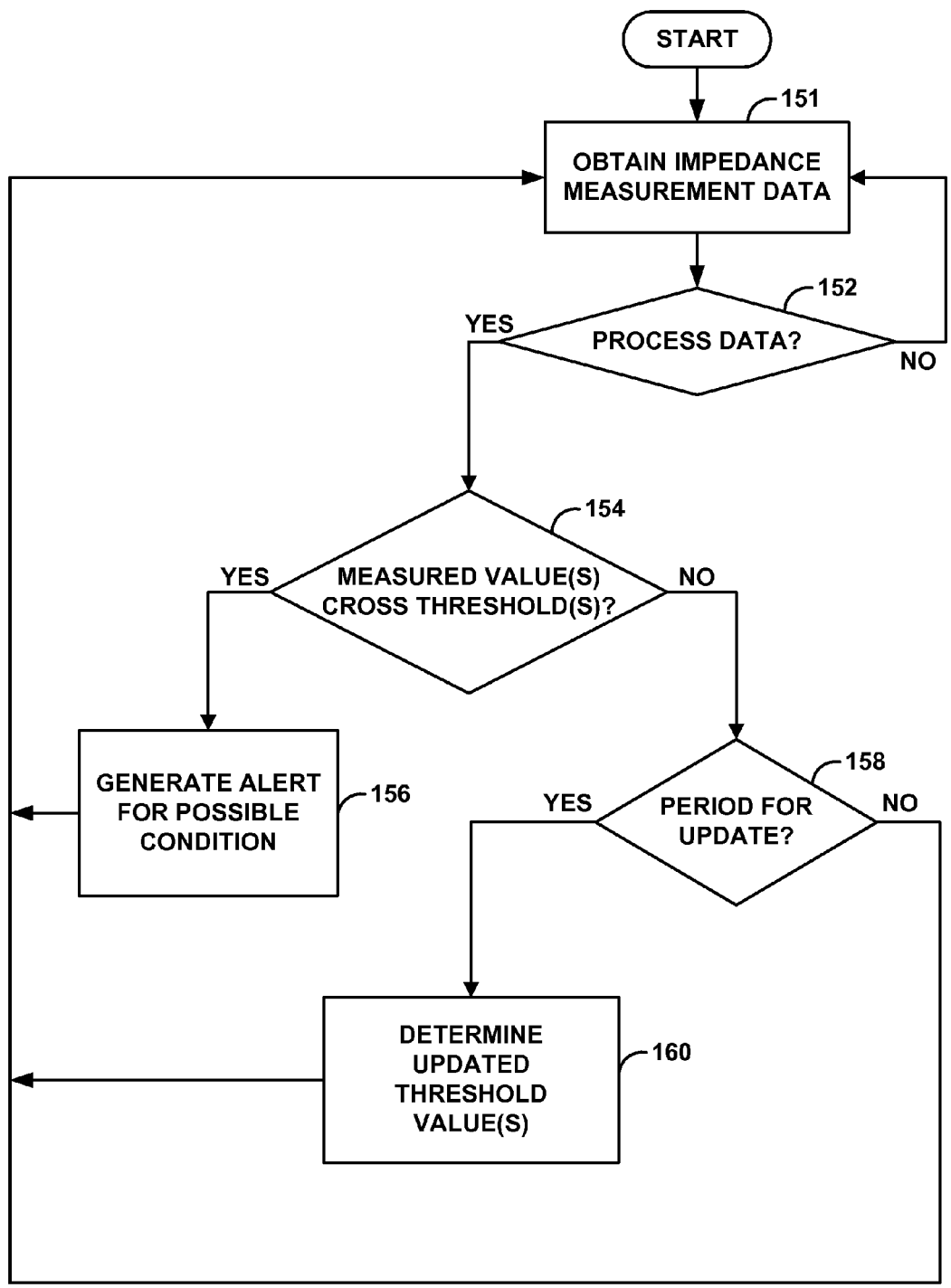
FIG. 8 is a flow diagram illustrating an example method that may be performed by the IMD or the programmer shown in FIG. 1 to cause an alert to be generated upon detection of a possible lead condition.

FIG. 8 is a flow diagram illustrating an example method that may be performed to cause an alert to be generated upon detection of a possible lead condition. In various examples, the method may be performed by IMD 16, external programmer 24, and/or an external device, such as device 132 (FIG. 8). For example, in certain cases, IMD 16 may store diagnostic data for one or more electrical paths associated with one or more electrodes that are coupled to IMD 16, including impedance measurement data, and then send this diagnostic data to external programmer 24 or to device 132 for processing in the manner shown in FIG. 8. In other cases, IMD 16 may directly process the diagnostic data, e.g., with processor 80 (FIG. 4). For illustration purposes only, it will be assumed in the subsequent description that IMD 16 performs the method shown in FIG. 8. It will also be assumed that IMD 16 performs this method with respect to one electrical path that includes at least one electrode of electrode leads 18, 20, or 22 that are coupled to IMD 16. Of course, IMD 16 may perform the method for each of plurality electrical paths that include one or more electrodes on the one or more leads.

IMD 16 obtains impedance measurement data for the electrical path (151). IMD 16 may, for example, measure and obtain impedance data for lead 18 by measuring impedance values for one or more electrical paths provided by lead 18, 20, or 22.

In the example of FIG. 8, IMD 16 obtains impedance measurement data for a particular sub-period. For example, IMD 16 may implement impedance measurement module 142 (FIG. 7). As described previously, impedance measurement module 142 may measure impedance values on an hourly basis, daily basis, weekly basis, or the like.

IMD 16 may then determine whether to process the data (152). For example, IMD 16 may utilize impedance value maintenance module 144 (FIG. 7) to determine whether the obtained impedance data should be processed or used to update any maintained values. If, for example, impedance value maintenance module 144 maintains maximum and minimum impedance values for a given week, and impedance measurement module 142 obtains impedance data on a daily basis (sub-period), impedance value maintenance module 144 may determine whether the maintained maximum or minimum impedance values should be updated with the daily measured impedance data. If not, impedance value maintenance module 144 may decide not to process the daily measured data, and wait to receive additional data from impedance measurement module 142 for a subsequent sub-period.

If, however, the measured data exceeds the current maximum impedance value, impedance value maintenance module 144 may process the measured data, and update the maximum impedance value with the measured data. Similarly, if the measured data is less than the current minimum impedance value, impedance value maintenance module 144 may process the measured data and update the minimum impedance value with the measured data.

When processing the measured data, IMD 16 may determine whether recently or newly measured impedance and/or range values cross a respective threshold (154). IMD 16 may implement threshold comparison module 148 (FIG. 7) to make such a determination. For example, module 148 may determine whether a newly measured maximum impedance value, such as a value measured on a particular day, exceeds a maximum threshold value. Module 148 may also determine whether a newly measured minimum impedance value falls below a minimum threshold value, and/or whether a newly measured range value exceeds a threshold range value.

IMD 16 may use one or more threshold values provided by threshold update module 146. These threshold values may include a maximum threshold value, a minimum threshold value, and/or a threshold range value. As described previously, threshold update module 146 may obtain values from impedance value/range calculator 149 and impedance variability calculator 147 to determine such threshold values. Threshold update module 146 may update various threshold values on a periodic (e.g., weekly) basis, but may provide the most current threshold values at any given time (e.g., daily) to threshold comparison module 148.

If any measured values cross (e.g., exceed) a respective threshold, IMD 16 may implement integrity indication module 150 to indicate a possible condition of the electrical path associated with an electrode lead based on the comparison of these values to the corresponding thresholds (156). In certain cases, integrity indication module 150 may generate an alert (such as a visual or audible alert) when one of the measured values exceeds a corresponding threshold value. In other cases, integrity indication module 150 may generate the alert when both the measured values exceed the corresponding threshold values, as is described in more detail below. The alert that may be generated indicates a possible lead condition.

If one or more of the measured values do not exceed the corresponding threshold values, IMD 16 checks whether it has reached a period for updating one or more threshold values (158). In one example, IMD 16 may only update these threshold values when one or more of the measured values do not exceed the corresponding, current threshold values. In the example of FIG. 8, IMD 16 updates these threshold values on a periodic basis based on a defined period (160). For example, IMD 16 may update these threshold values at the end of each day, end of each week, end of each month, or the like. If IMD 16 determines that it is time for an update (e.g., it is the end of the week), IMD 16 may implement impedance value/range calculator 149 (FIG. 7) of threshold update module 146 to determine, or calculate, updated values for impedance and/or range values based on the prior determined impedance and/or range values and newly measured impedance and/or range values. Impedance variability calculator 147 of threshold update module 146 may also determine, or calculate, updated impedance variability values based on the prior impedance variability values and newly measured impedance and/or range values. Threshold update module 146 may then use the output of impedance value/range calculator 149 and impedance variability calculator 147 to calculate updated threshold values.

As described previously, impedance value/range calculator 149 is capable of periodically computing impedance values and/or range values (e.g., mean values, median values, mode values, or other central tendency values) using the measured values that are provided by impedance measurement module 142. For example, if impedance measurement module 142 collects daily impedance data, impedance value/range calculator 149 may calculate an updated, weekly mean maximum impedance ("MEAN_MAX") value based upon the maximum impedance value for each week, and may calculate an updated, weekly mean minimum impedance value ("MEAN_MIN") based upon the minimum impedance value for each week.

In addition, impedance value/range calculator 149 is also capable of calculating a mean impedance range value ("MEAN_RANGE"). For example, an updated, weekly mean impedance range value may be calculated based upon both the maximum and minimum impedance value for each week.

Impedance variability calculator 147 may determine an impedance variability value. Impedance variability calculator 147 may calculate impedance variability values based on a difference between at least one of the impedance values/ranges and the determined impedance value at a particular point in time (e.g., at the end of a week). The impedance variability value indicates an expected level of variability for impedance measurements for the electrical path.

In one example, impedance variability calculator 147 may calculate variability factors for impedance and impedance range values measured over a given period of time (e.g., day or week). For example, impedance variability calculator 147 may calculate a mean maximum impedance variability value ("MAD_MAX") based on a difference between a weekly maximum impedance value and the mean maximum impedance value ("MEAN_MAX"). Impedance variability calculator 147 may calculate a mean impedance range variability value ("MAD_RANGE") based on a difference between a weekly impedance range value (weekly maximum-weekly minimum) and the mean impedance range value ("MEAN_RANGE"). Examples of these will be described in more detail below.

Threshold update module 146 may calculate the threshold value based on the determined impedance value and the impedance variability value. For example, if the determined impedance value is a mean maximum impedance value, module 146 may calculate the threshold value by adding the mean maximum impedance value to the impedance variability value (e.g., MEAN_MAX+MAD_MAX). If, however, the determined impedance value is a mean minimum value (when measuring minimum impedance values), threshold update module 146 may calculate a minimum threshold value by subtracting the impedance variability value from the mean minimum value. Threshold update module 146 may calculate the threshold range value based on the mean impedance range value and the impedance range variability value.

As shown in FIG. 8, IMD 16 may repeat various acts over multiple sub-periods (e.g., days) and periods (e.g., weeks). For example, IMD 16 may obtain impedance measurement data at 151 and potentially compare it against one or more thresholds on a daily basis, but may only update various thresholds and related state parameters (e.g., MEAN_MAX, MEAN_RANGE, MAD_MAX, MAD_RANGE) on a weekly basis. Daily and weekly are merely examples, and other periods for measurement, comparison, and threshold update are contemplated. By repeating various acts for multiple sub-periods and periods of time, IMD 16 is capable of continuously monitoring for possible lead conditions on a repeated basis, and is also capable of updating various state parameters to dynamically customize the impedance measurements for a given individual over time.

IMD 16 is also capable of performing the method shown in FIG. 8 for multiple electrical paths that are associated with one or more leads to identify any lead-related conditions with any number of different leads coupled to IMD 16. Each electrical path comprises one or more electrodes for the one or more leads. IMD 16 may utilize and store separate values for parameters such as MEAN_MAX, MEAN_RANGE, MAD_MAX, and/or MAD_RANGE for each electrical path that is to be checked using the method of FIG. 8, according to one embodiment.

Figure 9A:
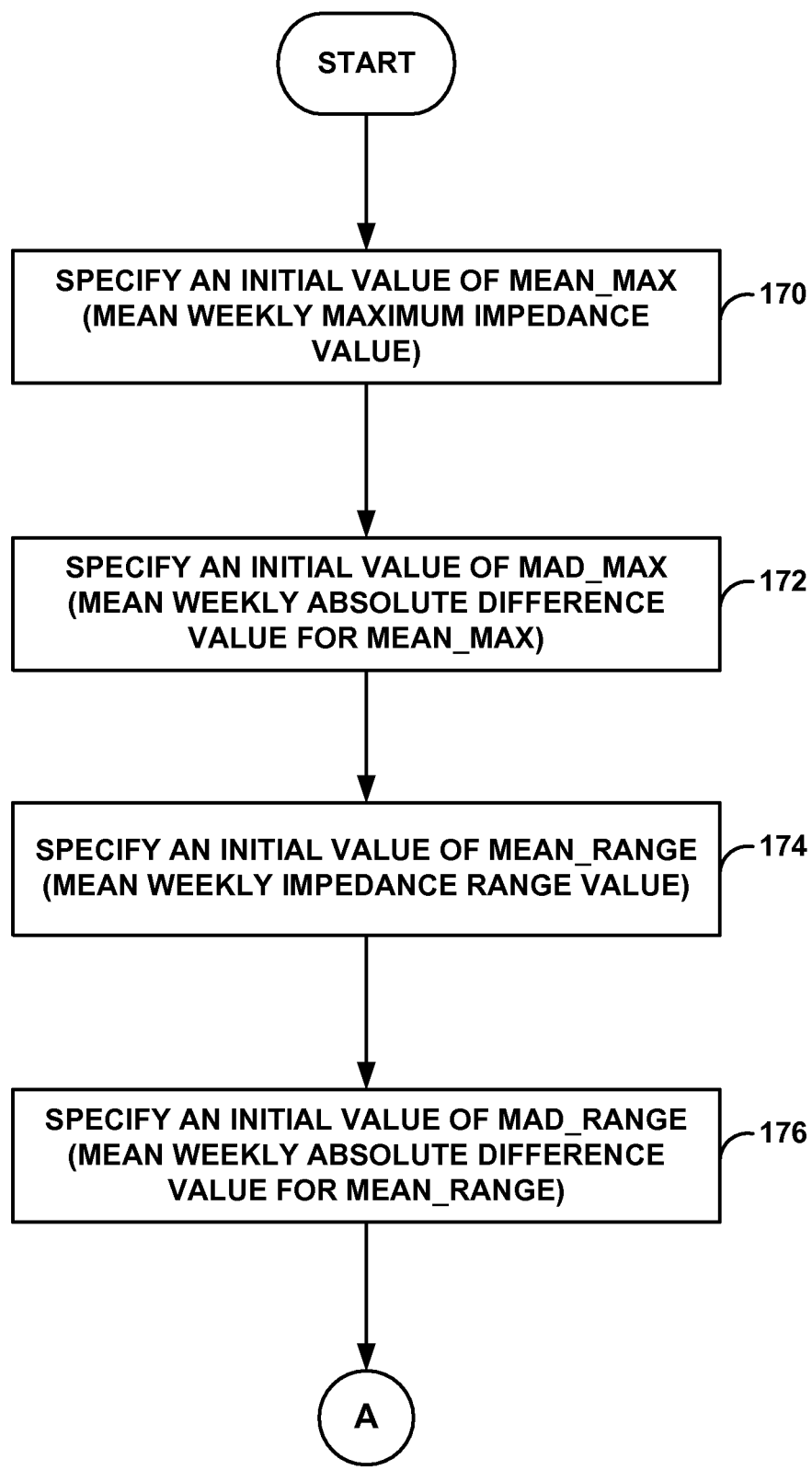
FIGS. 9A and 9B are flow diagrams that illustrate an example method to cause an alert to be generated upon detection of a possible lead condition.
Figure 9B:
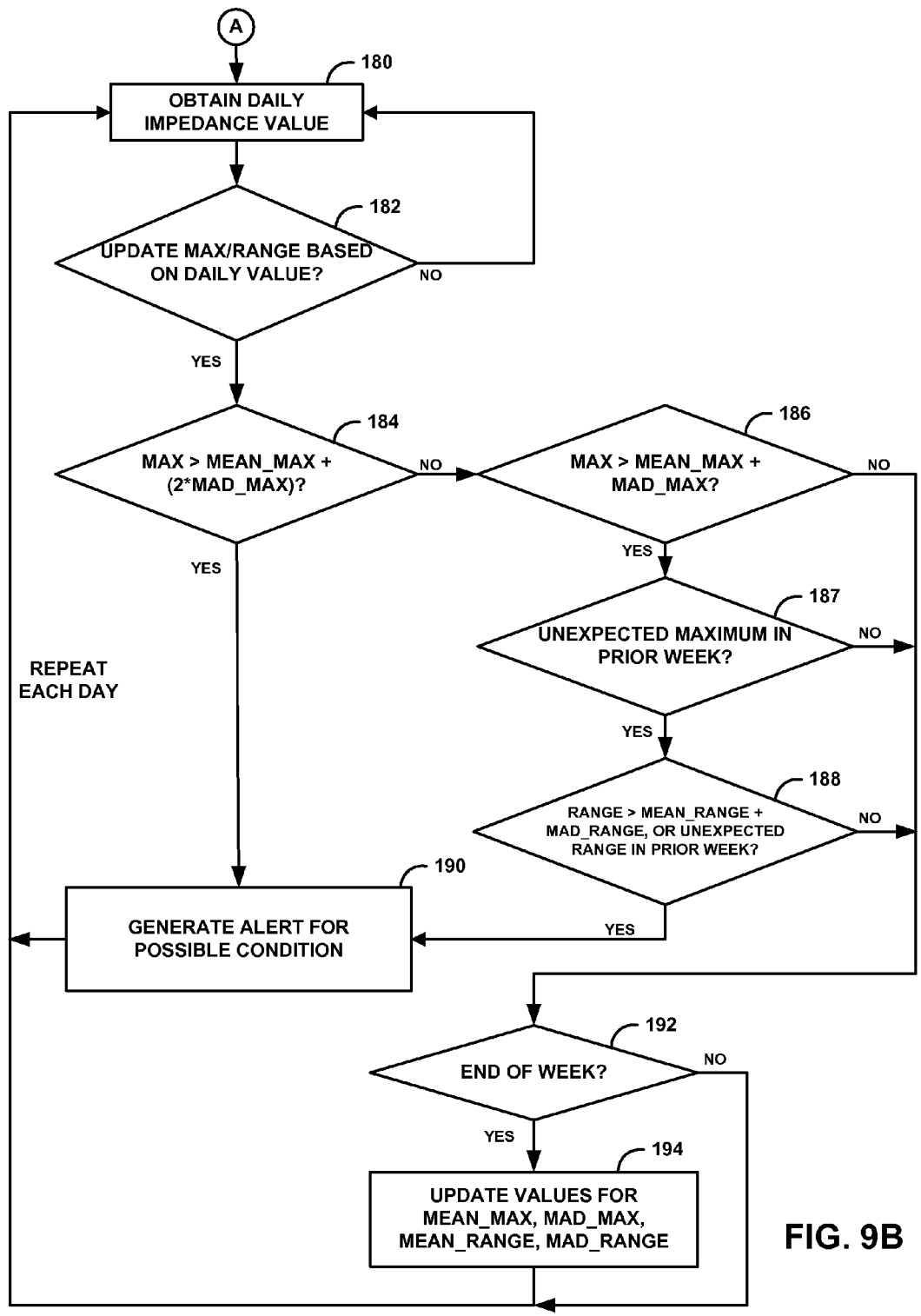

FIGS. 9A-9B show a flow diagram that illustrates a method that may be performed to cause an alert to be generated upon detection of a possible lead condition, according to one example. In this example, the method may be performed by IMD 16, external programmer 24, or by device 132 (FIG. 8). For illustration purposes only, it will be assumed in the subsequent description that IMD 16 performs the method shown in FIGS. 9A-9B. It will also be assumed that IMD 16 performs this method with respect to one electrical path associated with one of electrode leads 18, 20, or 22 that are coupled to IMD 16. Of course, IMD 16 may perform the method for each of plurality electrical paths that include one or more electrodes on the one or more leads. In certain cases, various acts of the method may be performed in part of entirely by another device, such as programmer 24 and/or external device 132. In the examples of FIGS. 9A-9B, various values are described as mean values. In other examples, however, various other forms of central tendency values (e.g., median values, mode values) may also be used and/or determined.

In the example shown in FIGS. 9A-9B, impedance values are measured at defined points in time, such as once every day (sub-period). Various other values, such as various calculated mean values, may be calculated and/or updated at defined points in time, as well, such as the end of each week (period). Initially, certain ones of these values are initialized to pre-set values for purposes of adaptation over time. For example, in FIG. 9A, IMD 16 specifies an initial value of MEAN_MAX (170). In this particular example, MEAN_MAX represents a mean weekly maximum impedance value. Initially, there may be no collected or measured maximum impedance values for an electrical path associated with lead 18, 20, or 22 (where the electrical path includes at least one electrode in or otherwise associated with the lead), and thus IMD 16 specifies an initial value for MEAN_MAX. As will be described below, MEAN_MAX is calculated, or updated, on a weekly basis, but its initial value may be pre-selected by IMD 16 for purposes of quickly adapting the value of MEAN_MAX over time. In some cases, IMD 16 may also specify an initial value for MEAN_MIN, which represents a mean weekly minimum impedance value.

IMD 16 may also specify an initial value of MAD_MAX (172). In this particular example, MAD_MAX represents a mean weekly absolute difference value between a weekly measured maximum impedance value and MEAN_MAX. As such, MAD_MAX indicates an estimate of variability of measured maximum impedance values with respect to MEAN_MAX.

IMD 16 may also specify an initial value of MEAN_RANGE (174). In this particular example, MEAN_RANGE represents a mean weekly impedance range value. The specified range may be defined as a difference between a maximum impedance value and a minimum impedance value in this example.

IMD 16 may also specify an initial value of MAD_RANGE (176). MAD_RANGE represents a mean weekly absolute difference value between a measured impedance range value (which is based upon the difference between maximum and minimum impedance values) and MEAN_RANGE. As such, MAD_RANGE indicates an estimate of variability of measure impedance range values with respect to MEAN_RANGE.

In one aspect, each of the specified initial values MEAN_MAX, MAD_MAX, MEAN_RANGE, and MAD_RANGE may comprise predetermined or defined values. These may be pre-stored on IMD 16, such as within memory 82 (FIG. 4) of IMD 16. In one example, impedance value maintenance module 144 and/or threshold update module 146 (FIG. 7) may specify the initial values of MEAN_MAX, MAD_MAX, MEAN_RANGE, and MAD_RANGE.

IMD 16 may subsequently determine multiple mean weekly maximum impedance values based on a plurality of initially measured maximum impedance values for an electrical path over a defined time period to obtain an adapted value of MEAN_MAX, in order to achieve more rapid, initial adaptation of MEAN_MAX. For example, IMD 16 may use an initial adaptation time period of ten weeks to achieve such initial adaptation. IMD 16 may determine multiple impedance variability values for MAD_MAX based on the plurality of initially measured maximum impedance values. For example, in some cases, IMD 16 may determine multiple impedance variability values for MAD_MAX based on differences between the plurality of initially measured maximum impedance values and the multiple determined values of MEAN_MAX over the defined time period to obtain an adapted value of MAD_MAX, in order to achieve more rapid, initial adaption of MAD_MAX. In addition, IMD 16 may use a similar approach (with respect to difference ranges for initially measured maximum and minimum impedance values over the defined time period) to determine adapted values of MEAN_RANGE and MAD_RANGE.

Referring to FIG. 9B, IMD 16 next obtains a daily impedance value (180). IMD 16 may implement impedance measurement module 142 to obtain daily impedance values. IMD 16 may then use impedance value maintenance module 144 to determine whether to update any maximum or range values based upon the daily impedance value (182). For example, impedance value maintenance module 144 may maintain running, updated values for MAX and RANGE. The MAX value represents the maximum impedance value for the current period (e.g., week in this example), and the RANGE value represents the difference, or range, between the maximum impedance value for the week (MAX) and the minimum impedance value for the week (MIN). On any given day, impedance value maintenance module 144 may determine whether the daily impedance value is greater than the current value of MAX or less than the current value of MIN. If not, the daily impedance value may be ignored. If the daily impedance value is greater than MAX, MAX is updated and set equal to the daily impedance value. If the daily impedance value is less than MIN, MIN is updated and set equal to the daily impedance value. If MAX and/or MIN are updated, the value of RANGE is also updated.

If MAX is updated, IMD 16 determines whether MAX is greater than (MEAN_MAX+2*MAD_MAX) (184) by using threshold comparison module 148. Module 148 attempts to determine if MAX is very unexpected based upon the current values of MEAN_MAX and MAD_MAX (which may be stored and provided by threshold update module 146). If MAX is greater than (MEAN_MAX+2*MAD_MAX), IMD 16 may cause integrity indication module 150 to generate an alert (190). The alert indicates a possible condition with the electrical path, which may be indicative of a lead condition. IMD 16 may, in some instances, communicate with programmer 24 to cause programmer 24 to generate the alert, which may comprise an audible or visual alert. In some instances, IMD 16 may automatically disable the electrical path and/or the lead, as well. In these cases, IMD 16 may temporarily or permanently disable the electrical path and/or the lead, or one or more electrodes coupled to the electrical path.

If MAX is less than or equal to (MEAN_MAX+2*MAD_MAX), threshold comparison module may next check whether MAX is greater than (MEAN_MAX+MAD_MAX) in the current week (186). If MAX is not greater than (MEAN_MAX+MAD_MAX) in the current week, IMD 16 determines whether to update the values of MEAN_MAX, MAD_MAX, MEAN_RANGE, and/or MAD_RANGE (192, 194), as described below.

If MAX is greater than (MEAN_MAX+MAD_MAX) in the current week, IMD 16 next determines whether there were any additional unexpected maximum impedance values that were identified in the prior week (187). Any additional unexpected maximum impedance values may have been identified in the prior week, for example, during a determination as to whether a maximum value in the prior week exceeded the MEAN_MAX value from the prior week plus the MAD_MAX value from the prior week. At this checkpoint, IMD 16 essentially determines whether there have been unexpected maximum impedance values measured in each of two consecutive weeks, in this example. If not, IMD 16 continues performing the method at act 192, as described below.

If, however, IMD 16 has identified unexpected maximum impedance values in each of two consecutive weeks, IMD 16 may then use threshold comparison module 148 to determine whether the RANGE value for the current week is greater than (MEAN_RANGE+MAD_RANGE) for the current week, or if there was a measured, unexpected range value in the prior week (based upon the values of MEAN_RANGE and MAD_RANGE of the prior week) (188). At this checkpoint, IMD 16 essentially determines whether there has been a measured, unexpected daily range value in one or both of the recent consecutive weeks. If not, IMD 16 continues performing the method, as described below.

If, however, IMD 16 has identified unexpected maximum impedance values in each of two consecutive weeks, and has also identified an unexpected impedance range value in one or both of these consecutive weeks, then IMD 16 may implement integrity indication module 150 to generate an alert that indicates a possible condition with a lead (190).

In some cases, when MAX exceeds (MEAN_MAX+MAD_MAX) or (MEAN_MAX+2*MAD_MAX) for multiple consecutive weeks, or a defined number of times, IMD

16 may increase the value of MAD_MAX and go through another adaptation time period to re-adapt the value of MAD_MAX. Similarly, when RANGE exceeds (MEAN_RANGE+MAD_RANGE) for multiple consecutive weeks, or a defined number of times, IMD 16 may increase the value of MAD_RANGE and go through another adaptation time period to re-adapt the value of MAD_RANGE.

IMD 16 may then determine whether the current day is the last day of the week (192). If not, IMD 16 waits to obtain another daily impedance value (180) to repeat the process shown in FIG. 9B the next (subsequent) day. If the current day is, however, the last day of the week, IMD 16 may implement threshold update module 146 to calculate updated values for MEAN_MAX, MAD_MAX, MEAN_RANGE, and MAD_RANGE (194). In one embodiment, mean value/range calculator 149 updates MEAN_MAX based upon the weekly maximum impedance value, MAX, and updates MEAN_RANGE based upon the weekly range, RANGE (i.e., difference between weekly maximum, MAX, and the weekly minimum, MIN). In one embodiment, impedance variability calculator 147 updates MAD_MAX based upon the difference MAX and MEAN_MAX, and updates MAD_RANGE based upon the difference between RANGE for the given week and MEAN_RANGE. In these embodiments, MAD_MAX and MAD_RANGE comprise mean values.

In one embodiment, the values of MAD_MAX, MEAN_MAX, MAD_RANGE, and MEAN_RANGE may be updated weekly based on the following equations:

$$\text{MAD\_MAX} = \text{mad}_{afM} * \text{MAD\_MAX} + ((1.0 - \text{mad}_{afM}) * FFM * (abs(z\max - \text{MEAN\_MAX})));$$

$$\text{MEAN\_MAX} = (\text{mean}_{afM} * \text{MEAN\_MAX} + (1.0 - \text{mean}_{afM}) * z\max);$$

$$\text{MAD\_RANGE} = \text{mad}_{afR} * \text{MAD\_RANGE} + ((1.0 - \text{mad}_{afR}) * FFR * (abs(\text{range}Z - \text{MEAN\_RANGE})));$$

$$\text{MEAN\_RANGE} = (\text{mean}_{afR} * \text{MEAN\_RANGE} + (1.0 - \text{mean}_{afR}) * \text{range}Z);$$

In these equations, zmax represents a weekly maximum value, and rangeZ represents the range value (MAX-MIN) for the given week. The values of madafM, FFM, meanafM, madafR, FFR, and meanafR are constant values, in some cases, that may be determined or calculated for optimization, as is shown and described in the pseudo-code further below. In some cases, the values of MAD_MAX and MAD_RANGE may also have lower-size and/or upper-size constraints for implementation, as is also shown in the pseudo-code.

In some cases, the values of MAD_MAX and/or MAD_RANGE may be constrained by upper and/or lower limits. For example, MAD_MAX may have upper and/or lower limits that are based on the value of MEAN_MAX. MAD_RANGE may have upper and/or lower limits that are based on the value of MEAN_RANGE.

After updating the values of MEAN_MAX, MEAN_RANGE, MAD_MAX, and MAD_RANGE, threshold update module 146 is capable of calculating updated threshold values. For example, threshold update module 146 may calculate one or more maximum impedance threshold values based upon MEAN_MAX and MAD_MAX (e.g., MEAN_MAX+2*MAD_MAX, MEAN_MAX+MAD_MAX). Threshold update module 146 may also calculate an updated threshold range value based upon MEAN_RANGE and MAD_RANGE (e.g., MEAN_RANGE+MAD_RANGE). After threshold update module 146 updates these various values, IMD 16 then waits to obtain another daily impedance value (180) to repeat the process for the next day.

Although the example shown in FIGS. 9A-9B illustrates integrity determinations made based on maximum values, IMD 16 is similarly capable of making integrity determinations based on minimum values for various parameters. For example, IMD 16 may calculate values for MEAN_MIN (mean weekly minimum impedance) and MAD_MIN (mean weekly absolute difference between a minimum impedance value and MEAN_MIN. IMD 16 may then implement similar checks and comparisons as shown in FIG. 9B, but may compare MIN (minimum impedance value for the week) to thresholds defined by (MEAN_MIN−2*MAD_MIN) or (MEAN_MIN−MAD_MIN), when attempting to identify possible electrical path and/or lead conditions. In addition, IMD 16 is also capable of combining the results of the algorithm shown in FIGS. 9A-9B with short interval count and non-sustained episode detection criteria to produce the overall prediction algorithm.

The example shown in FIGS. 9A-9B generates an alert if there is an unexpected maximum impedance value in two consecutive weeks, as well as an unexpected range impedance value in one of those weeks. However, in other scenarios, various other rules may be implemented for determining whether to generate such an alert. For example, IMD 16 may cause an alert to be generated if there is an unexpected maximum impedance value in five out of six consecutive weeks, and if there is also an unexpected range impedance value in any two of those weeks. In addition, although measured on a daily basis in the example above, the impedance values may be measured more or less frequently. For example, impedance values may be measured on an hourly basis, and, in addition, mean values may be calculated on a daily basis, rather than on a weekly basis. The examples above are provided for purposes of illustration only.

In addition, the method shown in FIGS. 9A-9B may be performed for multiple different electrical paths of one or more leads to identify any lead-related conditions with any number of different leads coupled to IMD 16. Each electrical path comprises one or more electrodes for the one or more leads. The various parameters, such as MAX, MIN, RANGE, MEAN_MAX, MEAN_RANGE, MAD_MAX, and MAD_RANGE may be determined, calculated, and stored for each individual electrical path that may be tested according to the method of FIGS. 9A-9B, according to one embodiment.

Figure 10:
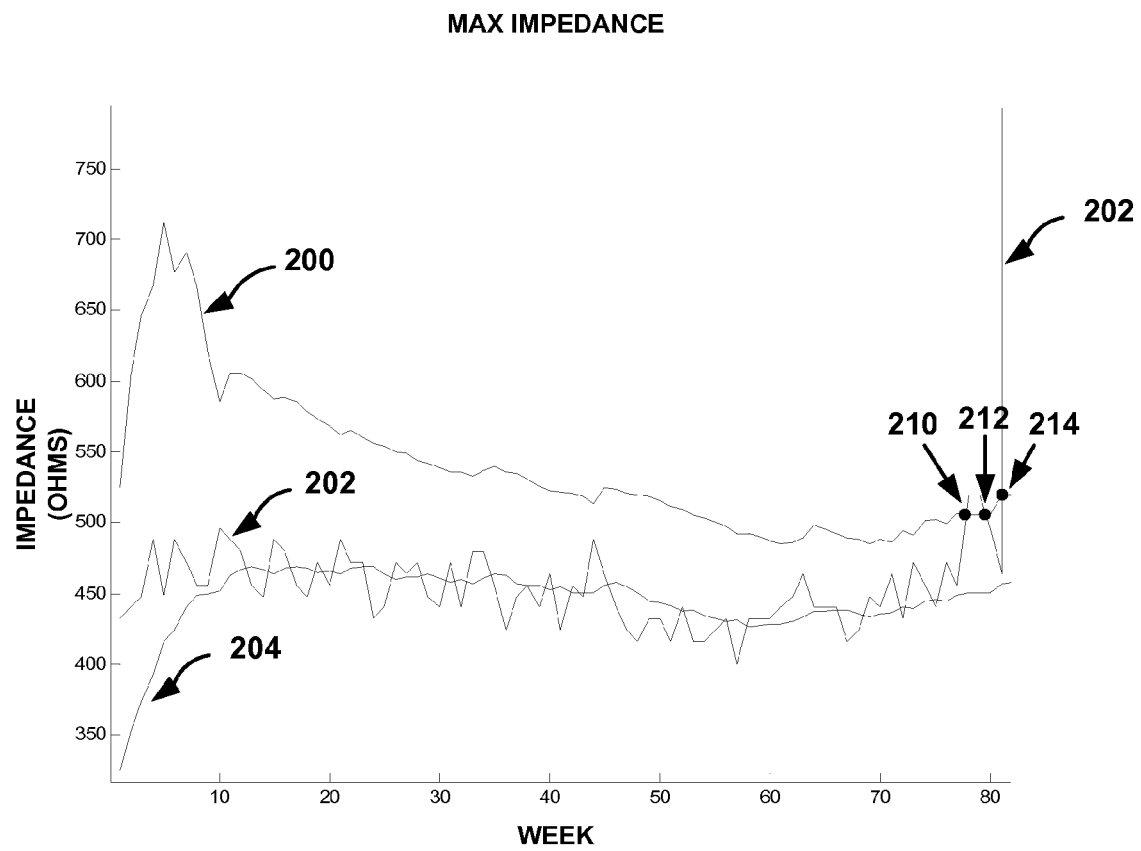
FIG. 10 is a graph illustrating examples of weekly measured maximum impedance values, mean values of the weekly maximum impedance values, and the weekly upper limits of the expected maximum impedance values.

FIG. 10 is a graph illustrating examples of weekly measured maximum impedance values in curve 202 (for each indicated week), running mean values of the weekly maximum impedance values in curve 204 (which may be updated each week), and the weekly upper limits of the expected maximum impedance values in curve 200. An upper limit, or threshold, for a given week in curve 200 may be determined by the mean value (MEAN_MAX) plus a factor determined by the estimated variability (e.g., MAD_MAX, 2*MAD_MAX).

As can be seen in curve 202 of FIG. 10, the weekly maximum impedance varies over time for the lead, such as lead 18, 20, or 22 that is coupled to IMD 16 implanted within patient 14. This may be due to several factors. For example, the maximum impedance value for any given week may vary based on the condition of patient 14, the activity level of patient 14, or other factors. As can also be seen in FIG. 10, the delta, or difference, between curve 200 and 202 decreases over time. Typically, during the first few weeks, the variability factor may be adapted and adjusted to the conditions within patient 14. The variability factor, or estimated variability (e.g., MAD_MAX), is a mean value that may be continually adjusted in each of the first few weeks. In FIG. 10, curve 200 has been substantially adapted, or adjusted, by week ten, in this example. Prior to week ten, which may be referred to as an initialization stage, the initial mean and variability values are being determined and adjusted, based on one embodiment.

Changes in the weekly values of measured maximum impedance values, shown in curve 202, and particularly larger changes, may be indicative of potential conditions of the lead, as opposed to variability within the lead based upon the condition of the patient 14. Sometime during week eighty one in the example of FIG. 10, the maximum impedance exceeds 10000 ohms. Curve 202 intersects curve 200 prior to this significant change, at point 214. However, the maximum impedance values in weeks seventy eight and seventy nine are unexpected, giving the potential for early warning of the possible condition. In week seventy eight, curve 202 intersects curve 200 at point 210, indicating that the maximum impedance value has exceeded the threshold value based on the mean maximum impedance value and the mean variability value (e.g., MEAN_MAX and MAD_MAX, MEAN_MAX and 2*MAD_MAX). In week seventy nine, curve 202 intersects curve 200 at point 212.

Figure 11:
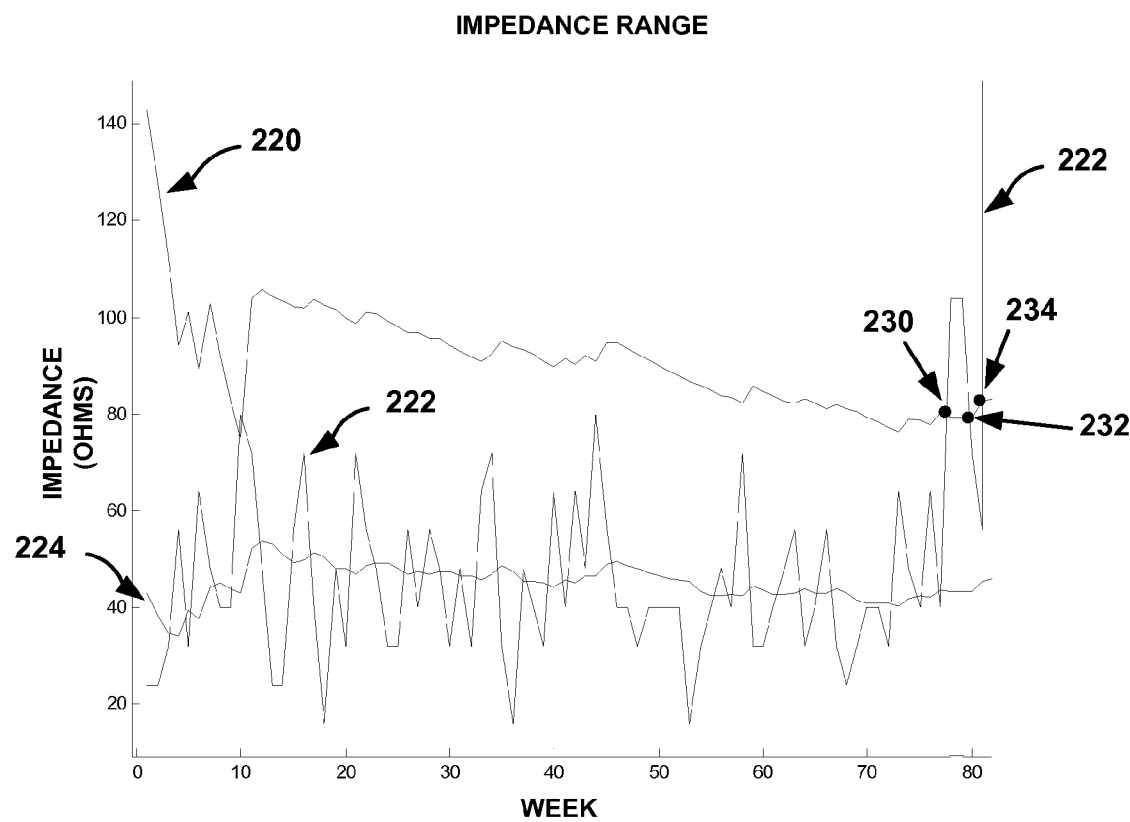
FIG. 11 is a graph illustrating examples of weekly measured range impedance values, mean values of the weekly range impedance value, and the weekly upper limits of the expected range impedance values.

FIG. 11 is a graph illustrating examples of weekly measured range (maximum–minimum) impedance values in curve 222 (for each indicated week), mean values of the weekly range impedance values in curve 224 (which may be updated each week), and the weekly upper limits of the expected range impedance values in curve 220. An upper limit, or threshold, for a given week in curve 220 may be determined by the mean value (e.g., MEAN_RANGE) plus a factor determined by the estimated variability (e.g., MAD_RANGE).

As can be seen in curve 222 of FIG. 11, the weekly range of impedance values may also vary over time for the lead. As can also be seen in FIG. 11 (and similar to FIG. 10), the delta, or difference, between curve 222 and 220 decreases over time. Curve 220 has been substantially adapted, or adjusted, by week ten, in this example. Prior to week ten, the initial mean and variability values are being determined and adjusted, based on one embodiment.

Changes in the weekly values of measured impedance range values, shown in curve 222, and particularly larger changes, may be indicative of potential conditions of the lead, as opposed to variability within the lead based upon the condition of the patient 14. Sometime during week eighty one in the example of FIG. 11, the impedance range exceeds 140 ohms. Curve 222 intersects curve 220 prior to this significant change, at point 234. However, the impedance range values in weeks seventy eight and seventy nine are unexpected, giving the potential for early indication of a possible condition. In week seventy eight, curve 222 intersects curve 220 at point 230, indicating that the impedance range value has exceeded the threshold value based on the mean impedance range value and the mean variability value (e.g., MEAN_RANGE and MAD_RANGE). In week seventy nine, curve 222 intersects curve 220 at point 232.

The techniques described in this disclosure, including those attributed to IMD 16, programmer 24, external device 132, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various embodiments of the disclosure have been described. These and other embodiments are within the scope of the claims.

Shown below is example pseudo-code that implements a lead impedance-change detection algorithm, based on one example embodiment (shown for purposes of illustration only). This code may be executed on all historical weekly impedance data to determine if an alert should be fired based on historical trends and to establish the following state variables: meanZmax (e.g., MEAN_MAX from above), madZmax (e.g., MAD_MAX from above), meanZrange (e.g., MEAN_RANGE from above), and madZrange (e.g., MAD_RANGE from above). Thereafter, the algorithm may be executed once daily to determine if alert conditions are met, but the state variables meanZmax, madZmax, meanZrange, and madZrange will only be updated once per week, after the weekly max and min are available. zmax and zmin indicate the weekly (or daily) maximum and minimum impedance values, respectively. Each day, the daily measured impedance value is compared to zmax and zmin to determine whether either of these values needs to be updated. zmax and zmin therefore indicate updated, running maximum and minimum impedance values, respectively, for the week.

The first portion of algorithm initialization involves initializing constants and variables (code lines 16 to 44). Each time that the code is executed (each day for new data or each week for historical data, for example), the variables LocationM and LocationR are set to zero. These are subsequently set to >0 if the zmax or RANGE (zmax–zmin) are unexpected.

The variables ZresetM and ZresetR are initially set to 10 and subsequently decrement for each week that the algorithm processes. When these variables are >0, the rate of adaptation of the expected ranges is greater (see lines 56-62 and 110-116 for selection of the adaptation rates), to aid in rapid adaptation to achieve the correct or optimum starting values of the state variables meanZmax, madZmax, meanZrange, madZrange. Also, when ZresetM or ZresetR are nonzero, the algorithm may not able to detect an impedance change, because the algorithm is not yet initialized. Finally, when ZresetM or ZresetR are nonzero, impedance values that are greater than the mean+mad are used to update the state variables (unless the zmax exceeds 1510 ohms or the RANGE (zmax−zmin) exceeds 151 ohms), whereas when ZresetM or ZresetR are zero, impedance values that are greater than the mean+mad are considered outliers and therefore are not used to update the state variables.

In line 65, the difference between the current value of zmax and meanZmax is determined. If this difference is greater than the allowed deviation (madZmax), then the current value of zmax is unexpected (line 66), and locationM is set to 1. If difference is greater than twice the allowed deviation (2*madZmax), then locationM is set to 2. The value of locationM will be used below to determine if a lead condition is suspected.

If the current value of zmax does not represent a complete week of data (i.e., this is a daily process, not a weekly process), the processing determines if the current RANGE (zmax−zmin) is unexpected. Lines 75 to 86 are used to update the state variables meanZmax and madZmax once each week. madZmax is constrained to be no larger than 50% of meanZmax, and no smaller than 5% of meanZmax.

Lines 91 to 103 manage the "lost" feature of the expected values of zmax. If there are four consecutive weeks where the zmax is unexpected, the algorithm then assumes that the expected values are lost (i.e., the zmax impedance has reached a new steady state that the algorithm will never accept). This results in a reset of the zmax expected values, enforced by setting ZresetM to 5 and enlarging the madZmax.

Line 117 sets the rangeZ to the difference between the weekly maximum and minimum impedance. For daily processing, this will be the difference between the maximum and minimum impedances measured so far in the week. For the first day of each week, rangeZ will be zero. At the end of the week, the final value of rangeZ will be determined for that week, and the state variables meanZrange and madZrange will then be updated as described below.

Line 122 determines the difference between the most recently obtained value of RANGE (zmax−zmin) and meanZrange. If this difference is greater than the allowed deviation (madZrange), then the current value of RANGE is unexpected (line 122), and locationR is set to 1. The value of locationR will be used below to determine if a lead condition is suspected.

If the current value of RANGE does not represent a complete week of data (i.e., this is a daily process, not a weekly process), the processing determines if a lead condition is suspected. Lines 130 to 139 are used to update the state variables meanZrange and madZrange once each week. The madZrange is constrained to be no larger than 3*meanZrange, and no smaller than 5% of meanZrange.

Lines 140 to 156 manage the "lost" feature of the RANGE (zmax−zmin). If there are four consecutive weeks where the RANGE is unexpected, the algorithm then assumes that the expected values for RANGE are lost (i.e., the RANGE has reached a new steady state that the algorithm will never accept). This results in a reset of the RANGE expected values, enforced by setting ZresetR to 5 and enlarging the madZrange.

In the pseudo-code, there are two criteria for identifying a lead-related condition: (1) there have been two consecutive weeks (or the prior week plus the current portion of a week) where the zmax impedance was unexpected AND the RANGE (zmax−zmin) was unexpected on either of these two occasions; or (2) the current value of the zmax impedance (determined each day) is greater than twice the allowed deviation from meanZmax, as indicated by locationM=2. When either of these two conditions are met, the impedance portion of the prediction algorithm is met (and can remain met for e.g., 60 days to allow opportunity for the other lead criteria, such as oversensing or detecting trends/events for non-sustained episodes, to be met). A timestamp could be recorded by the device at this point.

```
%
% Pseudocode for the Lead Impedance Change Detection Algorithm
%
% This code will be executed on all historical weekly impedance data upon
% download, to determine if an alert should be fired based on historical
% trends and to establish the state variables: meanZmax, madZmax,
% meanZrange, and madZrange. Thereafter, the algorithm will be executed
% daily to determine if alert conditions are met, but the state variables
% meanZmax, madZmax, meanZrange, and madZrange will only be updated once per
% week, after the weekly max and min are available.
% "zmax" and "zmin" indicate the weekly (or daily) maximum and minimum
% impedance, respectively
% <<<<<<<<<<<<<<<<< INITIAL VALUES >>>>>>>>>>>>>>>>>>>>
% CONSTANTS
% optimal detection parameters for the MAX impedance trend
MEANAFM = 0.85;
MADAFM = 0.93;
FFM = 3.8;
MINMADM = .05;
MAXMADM = .5;
    % optimal detection parameters for the RANGE impedance trend
    MEANAFR = 0.93;
    MADAFR = 0.97;
    FFR = 3.0;
    MINMADR = .05;
    MAXMADR = 3;
    % variables for MAX
    % start of a new record, initialize variables
    meanZmax = 325; % initial value is an important impact on performance!
    % 325 was determined to be the optimal starting point
    madZmax = 200;
    ZresetM = 10; % first 10 weeks used to initialize
    ZlostM = 0; % keeps track of successive weeks unexpected
```

```
% variables for RANGE
meanZrange = 43; % determined to be the optimal starting point
madZrange = 100;
ZresetR = 10; % first 10 weeks used to initialize
ZlostR = 0; % keeps track of successive weeks unexpected
% end of initial variables.
% <<<<<<<<<<<<<<< CODE FOR DAILY EXECUTION BELOW >>>>>>>>>>>>>>>>>>>>
% Code below will update the state variables
% and check for alert conditions
locationM = 0; % set to 1 if unexpected, 2 if very unexpected
locationR = 0; % set to 1 if unexpected
% <<<<< start with processing the MAX impedance >>>>>>
% determine the adaptation factors for mean and mad
if (ZresetM) % adaptation is faster during initialization
    meanafM = 0.75;
    madafM= 0.75;
else
    meanafM = MEANAFM;
    madafM = MADAFM;
end
% determine if the current MAX is expected
if (~(ZresetM && (zmax > 1510)))
    diff = zmax − meanZmax;
    if (diff > madZmax)
        locationM = 1; % unacceptable rise in impedance range
    end
    if (diff > 2*madZmax)
        locationM = 2; % more than twice out of expected range
    end
    % skip to the end of MAX processing code for daily execution, but
    % continue processing for the weekly execution (when the final weekly
    % MAX is known)
    diff = abs(diff);
    if (~locationM || ZresetM)
        madZmax = madafM*madZmax +((1.0−madafM)*FFM*diff);
        % constrain lower size of madZmax
        if (madZmax < MINMADM*meanZmax)
            madZmax = MINMADM*meanZmax;
        end
        % constrain upper size of madZmax
        if ((madZmax > MAXMADM*meanZmax) && (~ZresetM))
            madZmax = MAXMADM*meanZmax;
        end
        meanZmax = (meanafM*meanZmax + (1.0−meanafM)* zmax);
        if (ZresetM)
            ZresetM = ZresetM −1;
        end
    end
    % update the ZlostM counter
    if (locationM)
        ZlostM = ZlostM + 1;
    end
    if ((~locationM) && (ZlostM))
        ZlostM = ZlostM − 1;
    end
    if ((ZlostM >= 4) && locationM)
        ZresetM = 5; % reset because we are "lost"
        if madZmax < 200, % broaden expected range.
            madZmax = 200;
        end
    end
end % if not (reset & zmax > 1510)
% end of processing MAX impedance
% <<<<<< move on to processing the impedance RANGE >>>>>>
% determine the adaptation factors for mean and mad
if (ZresetR) % adaptation is faster during initialization
    meanafR = 0.75;
    madafR = 0.75;
else
    meanafR = MEANAFR;
    madafR = MADAFR;
end
rangeZ = zmax−zmin; % on the first day of a new week, rangeZ = 0.
% Thereafter, range = the max−min of the available days of that week
% determine if the current RANGE is expected
if (~(ZresetR && (rangeZ > 151))) % skip values of impedance > 151 if in reset mode
    diff = rangeZ − meanZrange;
    if (diff > madZrange)
        locationR = 1; % unexpected impedance range
    end
```

```
-continued

% skip to the end of RANGE processing code for daily execution, but
% continue processing for the weekly execution (when the final weekly RANGE
% is known).
diff = abs(diff);
if (~locationR || ZresetR)
    madZrange = madafR*madZrange +((1.0-madafR)*FFR*diff);
    % constrain lower size of madZrange
    if (madZrange < MINMADR*meanZrange)
        madZrange = MINMADR*meanZrange;
    end
    % constrain upper size of madZrange
    if ((madZrange > MAXMADR*meanZrange) && (~ZresetR))
        madZrange = MAXMADR*meanZrange;
    end
    meanZrange = (meanafR*meanZrange + (1.0-meanafR)* rangeZ);
    if (ZresetR)
        ZresetR = ZresetR − 1;
    end
end
% update the ZlostR counter
if (locationR)
    ZlostR = ZlostR + 1;
end
if ((~locationR) && (ZlostR))
    ZlostR = ZlostR − 1;
end
if ((ZlostR >= 4) && locationR)
    ZresetR = 5; % reset because we are "lost"
    if madZrange < 100, % broaden expected range.
        madZrange = 100;
    end
end
end % if not (reset & range > 151)
% end of processing to determine if the RANGE is unexpected
% <<<<<<<<<<<< finally, determine if alert conditions are met >>>>>>>>>>>>
% alert conditions are met if
% EITHER:
%     two consecutive weeks with unexpected MAX (locationM = 1)
%     AND
%     either one of these 2 weeks with unexpected RANGE (locationR = 1)
% OR
%     any single week with MAX > meanZmax+2*madZmax (locationM = 2)
%
% for daily processing, the current day's results substitute for the most
% recent week.
%
% NOTE that the definition of "unexpected" comes from the "locationR" and
% "locationM" variables, such that the current day impedance is judged
% against the prior mean + mad, not against the mean + mad that were
% just updated from that same recently-obtained impedance.
```

The invention claimed is:

1. A method comprising:

obtaining a plurality of measured impedance values for an electrical path that are measured over multiple periods of time, wherein the electrical path comprises a plurality of electrodes for at least one of stimulation or sensing;

obtaining a central tendency of the plurality of measured impedance values for the electrical path;

determining an impedance value for the electrical path based on the central tendency;

determining an impedance variability value based on at least a difference between one of the plurality of measured impedance values and the determined impedance value, wherein the one of the plurality of measured impedance values comprises either a maximum or a minimum impedance value measured during one of the multiple periods of time, and wherein the impedance variability value indicates an expected level of variability for impedance measurements for the electrical path;

determining an impedance threshold value based on the determined impedance value and the impedance variability value;

comparing a newly measured impedance value for the electrical path to the impedance threshold value; and indicating a possible condition of the electrical path based on the comparison.

2. The method of claim 1, wherein the plurality of measured impedance values comprises a first plurality of measured impedance values, wherein the electrical path comprises a first electrical path, wherein the central tendency comprises a first central tendency, wherein the impedance value comprises a first impedance value, wherein the impedance variability value comprises a first impedance variability value, wherein the multiple periods of time comprises a first multiple periods of time, and wherein the threshold value comprises a first threshold value, the method further comprising:

obtaining a second plurality of measured impedance values for a second electrical path that are measured over a second multiple periods of time;

obtaining a second central tendency of the second plurality of measured impedance values for the second electrical path;

determining a second impedance value for the second electrical path based on the second central tendency;

determining a second impedance variability value based on a difference between at least one of the second plurality of measured impedance values and the determined second impedance value, wherein the one of the second plurality of measured impedance values comprises either a maximum or a minimum impedance value measured during one of the second multiple periods of time;

determining a second threshold value based on the second determined impedance value and the second impedance variability value;

comparing a newly measured impedance value for the second electrical path to the second threshold value; and indicating a possible condition of the second electrical path based on the comparison to the second threshold value.

3. The method of claim 1, further comprising:
determining multiple impedance values based on the plurality of measured impedance values for the electrical path over a defined time period the multiple periods of time to obtain an adapted value of the determined impedance value; and determining multiple impedance variability values based on differences between the plurality of measured impedance values and the multiple determined impedance values over the multiple periods of time to obtain an adapted value of the impedance variability value.

4. The method of claim 1, wherein indicating the possible condition comprises generating an indication to a user of the possible condition.

5. The method of claim 1, wherein:
determining the impedance value comprises determining a mean maximum impedance value based on a central tendency of maximum impedance values of the plurality of measured impedance values for the electrical path that are measured over the multiple periods of time;

determining the impedance variability value comprises determining a maximum impedance variability value based on a difference between at least one of the maximum impedance values of the plurality of measured impedance values and the mean maximum impedance value at a particular point in time;

determining the impedance threshold value comprises determining a maximum impedance threshold value based on the mean maximum impedance value and the maximum impedance variability value; and comparing the newly measured impedance value comprises comparing a newly measured maximum impedance value to the maximum impedance threshold value.

6. The method of claim 5, wherein comparing the newly measured maximum impedance value to the maximum impedance threshold value comprises determining whether the newly measured maximum impedance value exceeds the maximum impedance threshold value.

7. The method of claim 1, further comprising:
when the newly measured impedance value is below the impedance threshold value and comprises either the maximum or the minimum impedance value measured during one of the multiple periods of time, determining an updated impedance variability value based on the impedance variability value and a difference between the newly measured impedance value and the determined impedance value, such that impedance variability values may adapt over time; and when the newly measured impedance value is below the impedance threshold value and comprises either the maximum or the minimum impedance value measured during one of the multiple periods of time, determining an updated impedance value based on the determined impedance value and the newly measured impedance value, such that determined impedance values may adapt over time.

8. The method of claim 7, further comprising:
repeating, over the multiple time periods of time, the determining of the impedance value, the determining of the impedance variability value, the determining of the impedance threshold value, the comparing of the newly measured impedance value to the impedance threshold value, the determining of the updated impedance variability value, and the determining of the updated impedance value.

9. The method of claim 8, wherein indicating the possible condition occurs when multiple newly measured impedance values have each crossed a respective impedance threshold value during at least two of the multiple time periods of time.

10. The method of claim 1, further comprising:
constraining the impedance variability value based on the determined impedance value.

11. The method of claim 1, further comprising:
obtaining a central tendency of a plurality of difference ranges between maximum and minimum impedance values measured over the multiple periods of time;

determining an impedance range value for the electrical path based on the central tendency of the plurality of difference ranges;

determining an impedance range variability value based on a difference between the determined impedance range value and at least one of the plurality of difference ranges;

determining an impedance threshold range value based on the determined impedance range value and the impedance range variability value; and comparing newly measured maximum and minimum impedance values for the electrical path to the impedance threshold range value, wherein indicating the possible condition of the electrical path is further based on the comparison of the newly measured maximum and minimum impedance values to the impedance threshold range value.

12. The method of claim 11, further comprising:
determining an updated impedance range variability value based on the impedance range variability value and a difference between the determined impedance range value and the newly measured maximum and minimum impedance values, such that impedance range variability values may adapt over time; and determining an updated impedance range value based on the determined impedance range value and the newly measured maximum and minimum impedance values, such that determined impedance range values may adapt over time.

13. The method of claim 1, wherein at least one of the plurality of electrodes is located on an implantable medical lead coupled to an implantable medical device.

14. An implantable medical device comprising:
a module configured to measure a plurality of impedance values for an electrical path associated with at least one implantable lead, wherein the plurality of measured impedance values are measured over multiple periods of time and, wherein the electrical path comprises a plurality of electrodes for at least one of patient stimulation or sensing; and a processor configured to:
obtain a central tendency of the plurality of measure impedance values for the electrical path;

determine an impedance value for the electrical path based on the central tendency;

determine an impedance variability value based on at least a difference between one of the plurality of measured impedance values and the determined impedance value, wherein the one of the plurality of measured impedance values comprises either a maximum or a minimum impedance value measured during one of the multiple periods of time, and wherein the impedance variability value indicates an expected level of variability for impedance measurements for the electrical path;

determine an impedance threshold value based on the determined impedance value and the impedance variability value;

compare a newly measured impedance value for the electrical path to the impedance threshold value; and indicate a possible condition of the electrical path based on the comparison.

15. The implantable medical device of claim 14, further comprising a stimulation generator configured to deliver stimulation via the at least one implantable lead, wherein at least one of the plurality of electrodes is located on the at least one implantable lead.

16. The implantable medical device of claim 14, wherein the plurality of measured impedance values comprises a first plurality of measured impedance values, wherein the electrical path comprises a first electrical path, wherein the central tendency comprises a first central tendency, wherein the impedance value comprises a first impedance value, wherein the impedance variability value comprises a first impedance variability value, wherein the multiple periods of time comprises a first multiple periods of time, wherein the threshold value comprises a first threshold value, and wherein the processor is further configured to:

obtain a second plurality of measured impedance values for a second electrical path that are measured over a second multiple periods of time;

obtain a second central tendency of the second plurality of measured impedance values for the second electrical path;

determine a second impedance value for the second electrical path based on the second central tendency;

determine a second impedance variability value based on a difference between at least one of the second plurality of measured impedance values and the determined second impedance value, wherein the one of the second plurality of measured impedance values comprises either a maximum or a minimum impedance value measured during one of the second multiple periods of time;

determine a second threshold value based on the second determined impedance value and the second impedance variability value;

compare a newly measured impedance value for the second electrical path to the second threshold value; and indicate a possible condition of the second electrical path based on the comparison to the second threshold value.

17. The implantable medical device of claim 14, wherein the processor is further configured to:

determine multiple impedance values based on the plurality of measured impedance values for the electrical path over a defined time period the multiple periods of time to obtain an adapted value of the determined impedance value; and determine multiple impedance variability values based on differences between the plurality of measured impedance values and the multiple determined impedance values over the multiple periods of time to obtain an adapted value of the impedance variability value.

18. The implantable medical device of claim 14, wherein the processor is configured to generate an indication to a user of the possible condition.

19. The implantable medical device of claim 14, wherein:

the processor is configured to determine the impedance value at least by determining a mean maximum impedance value based on a central tendency of maximum impedance values of the plurality of measured impedance values for the electrical path that are measured over the multiple periods of time;

the processor is configured to determine the impedance variability value at least by determining a maximum impedance variability value based on a difference between at least one of the maximum impedance values of the plurality of measured impedance values and the mean maximum impedance value at a particular point in time;

the processor is configured to determine the impedance threshold value at least by determining a maximum threshold value based on the mean maximum impedance value and the maximum impedance variability value; and the processor is configured to compare the newly measured impedance value at least by comparing a newly measured maximum impedance value to the maximum impedance threshold value.

20. The implantable medical device of claim 19, wherein the processor is configured to compare the newly measured maximum impedance value to the maximum impedance threshold value at least by determining whether the newly measured maximum impedance value exceeds the maximum impedance threshold value.

21. The implantable medical device of claim 14, wherein the processor is further configured to:

determine an updated impedance variability value based on the impedance variability value and a difference between the newly measured impedance value and the determined impedance value when the newly measured impedance value is below the impedance threshold value and comprises either the maximum or the minimum impedance value measured during one of the multiple periods of time, such that impedance variability values may adapt over time; and determine an updated impedance value based on the determined impedance value and the newly measured impedance value when the newly measured impedance value is below the impedance threshold value and comprises either the maximum or the minimum impedance value measured during one of the multiple periods of time, such that determined impedance values may adapt over time.

22. The implantable medical device of claim 21, wherein the processor is further configured to:

repeat, over the multiple time periods of time, the determining of the impedance value, the determining of the impedance variability value, the determining of the impedance threshold value, the comparing of the newly measured impedance value to the impedance threshold value, the determining of the updated impedance variability value, and the determining of the updated impedance value.

23. The implantable medical device of claim 22, wherein the processor is configured to indicate the possible condition when multiple newly measured impedance values have each crossed a respective impedance threshold value during at least two of the multiple periods of time.

24. The implantable medical device of claim 14, wherein the processor is further configured to constrain the impedance variability value based on the determined impedance value.

25. The implantable medical device of claim 14, wherein the processor is further configured to:
   obtain a central tendency of a plurality of difference ranges between maximum and minimum impedance values measured over the multiple periods of time;
   determine an impedance range value for the lead based on the central tendency of the plurality of difference ranges between maximum and minimum impedance values measured over the multiple periods of time;
   determine an impedance range variability value based on a difference between the determined impedance range value and at least one of the plurality of difference ranges;
   determine an impedance threshold range value based on the determined impedance range value and the impedance range variability value; and
   compare newly measured maximum and minimum impedance values for the electrical path to the impedance threshold range value,
   wherein the processor is further configured to indicate the possible condition of the electrical path based on the comparison of the newly measured maximum and minimum impedance values to the impedance threshold range value.

26. The implantable medical device of claim 25, wherein the processor is further configured to:
   determine an updated impedance range variability value based on the impedance range variability value and a difference between the determined impedance range value and the newly measured maximum and minimum impedance values, such that impedance range variability values may adapt over time; and
   determine an updated impedance range value based on the determined impedance range value and the newly measured maximum and minimum impedance values, such that determined impedance range values may adapt over time.

27. A system comprising:
   a module configured to receive a plurality of impedance values for an electrical path associated with at least one lead, wherein the plurality of measured impedance values are measured over multiple periods of time and, wherein the electrical path comprises a plurality of electrodes for at least one of patient stimulation or sensing; and
   one or more processors configured to:
      obtain a central tendency of the plurality of measured impedance values for the electrical path;
      determine an impedance value for the electrical path based on the central tendency;
      determine an impedance variability value based on at least a difference between one of the plurality of measured impedance values and the determined impedance value, wherein the one of the plurality of measured impedance values comprises either a maximum or a minimum impedance value measured during one of the multiple periods of time, and wherein the impedance variability value indicates an expected level of variability for impedance measurements for the electrical path;
      determine an impedance threshold value based on the determined impedance value and the impedance variability value;
      compare a newly measured impedance value for the electrical path to the impedance threshold value; and
      indicate a possible condition of the electrical path based on the comparison.

28. The system of claim 27, further comprising a user interface module configured to display an alarm that indicates the possible condition of the electrical path.

29. The system of claim 27, wherein the plurality of measured impedance values comprises a first plurality of measured impedance values, wherein the electrical path comprises a first electrical path, the central tendency comprises a first central tendency, wherein the impedance value comprises a first impedance value, wherein the impedance variability value comprises a first impedance variability value, wherein the multiple periods of time comprises a first multiple periods of time, wherein the threshold value comprises a first threshold value, and wherein the one or more processors are further configured to:
   obtain a second plurality of measured impedance values for a second electrical path that are measured over a second multiple periods of time;
   obtain a second central tendency of the second plurality of measured impedance values for the second electrical path;
   determine a second impedance value for the second electrical path based on the second central tendency;
   determine a second impedance variability value based on at least a difference between one of the second plurality of measured impedance values and the determined second impedance value, wherein the one of the second plurality of measured impedance values comprises either a maximum or a minimum impedance value measured during one of the second multiple periods of time;
   determine a second threshold value based on the second determined impedance value and the second impedance variability value;
   compare a newly measured impedance value for the second electrical path to the second threshold value; and
   indicate a possible condition of the second electrical path based on the comparison to the second threshold value.

30. The system of claim 27, wherein the one or more processors are further configured to:
   determine multiple impedance values based on the plurality of measured impedance values for the electrical path over a defined time period the multiple periods of time to obtain an adapted value of the determined impedance value; and
   determine multiple impedance variability values based on differences between the plurality of measured impedance values and the multiple determined impedance values over the multiple periods of time to obtain an adapted value of the impedance variability value.

31. The system of claim 27, wherein the one or more processors are configured to generate an indication to a user of the possible condition.

32. The system of claim 27, wherein:
   the one or more processors are configured to determine the impedance value at least by determining a mean maximum impedance value based on a central tendency of maximum impedance values of the plurality of measured impedance values for the electrical path that are measured over the multiple periods of time;
   the one or more processors are configured to determine the impedance variability value at least by determining a maximum impedance variability value based on a difference between at least one of the maximum impedance values of the plurality of measured impedance values and the mean maximum impedance value at a particular point in time;

the one or more processors are configured to determine the impedance threshold value at least by determining a maximum threshold value based on the mean maximum impedance value and the maximum impedance variability value; and the one or more processors are configured to compare the newly measured impedance value at least by comparing a newly measured maximum impedance value to the maximum impedance threshold value.

33. The system of claim 32, wherein the one or more processors are configured to compare the newly measured maximum impedance value to the maximum impedance threshold value at least by determining whether the newly measured maximum impedance value exceeds the maximum impedance threshold value.

34. The system of claim 27, wherein the one or more processors are further configured to:
determine an updated impedance variability value based on the impedance variability value and a difference between the newly measured impedance value and the determined impedance value when the newly measured impedance value is below the impedance threshold value and comprises either the maximum or the minimum impedance value measured during one of the multiple periods of time, such that impedance variability values may adapt over time; and
determine an updated impedance value based on the determined impedance value and the newly measured impedance value when the newly measured impedance value is below the impedance threshold value and comprises either the maximum or the minimum impedance value measured during one of the multiple periods of time, such that determined impedance values may adapt over time.

35. The system of claim 34, wherein the one or more processors are further configured to:
repeat, over the multiple periods of time, the determining of the impedance value, the determining of the impedance variability value, the determining of the impedance threshold value, the comparing of the newly measured impedance value to the impedance threshold value, the determining of the updated impedance variability value, and the determining of the updated impedance value.

36. The system of claim 35, wherein the one or more processors are configured to indicate the possible condition when multiple newly measured impedance values have each crossed a respective impedance threshold value during at least two of the multiple periods of time.

37. The system of claim 27, wherein the one or more processors are further configured to constrain the impedance variability value based on the determined impedance value.

38. The system of claim 27, wherein the one or more processors are further configured to:
obtain a central tendency of a plurality of difference ranges between maximum and minimum impedance values measured over the multiple periods of time;
determine an impedance range value for the lead based on the central tendency of the plurality of difference ranges;
determine an impedance range variability value based on differences between the determined impedance range value and at least one of the plurality of difference ranges;

determine an impedance threshold range value based on the determined impedance range value and the impedance range variability value; and
compare newly measured maximum and minimum impedance values for the electrical path to the impedance threshold range value,
wherein the one or more processors are further configured to indicate the possible condition of the electrical path based on the comparison of the newly measured maximum and minimum impedance values to the impedance threshold range value.

39. The system of claim 38, wherein the one or more processors are further configured to:
determine an updated impedance range variability value based on the impedance range variability value and a difference between the determined impedance range value and the newly measured maximum and minimum impedance values, such that impedance range variability values may adapt over time; and
determine an updated impedance range value based on the determined impedance range value and the newly measured maximum and minimum impedance values, such that determined impedance range values may adapt over time.

40. A system comprising:
an impedance measurement module configured to receive a plurality of measured impedance values for an electrical path associated with at least one medical lead, wherein the plurality of measured impedance values are measured over multiple periods of time and, wherein the electrical path comprises a plurality of electrodes for at least one of patient stimulation or sensing;
a threshold update module configured to obtain a central tendency of the plurality of measured impedance values for the electrical path, to determine an impedance value for the electrical path based on the central tendency, to determine an impedance variability value based on at least a difference between one of the plurality of measured impedance values and the determined impedance value, wherein the one of the plurality of measured impedance values comprises either a maximum or a minimum impedance value measured during one of the multiple periods of time, wherein the impedance variability value indicates an expected level of variability for impedance measurements for the electrical path, and wherein the threshold update module is further configured to determine an impedance threshold value based on the determined impedance value and the impedance variability value;
a threshold comparison module configured to compare a newly measured impedance value for the electrical path to the impedance threshold value; and
an integrity indication module configured to indicate a possible condition of the electrical path based on the comparison.

41. A non-transitory computer-readable storage medium comprising instructions for causing one or more processors to:
obtain a plurality of measured impedance values for an electrical path that are measured over multiple periods of time, wherein the electrical path comprises a plurality of electrodes for at least one of stimulation or sensing;
obtain a central tendency of the plurality of measured impedance values for the electrical path;
determine an impedance value for the electrical path based on the central tendency;

determine an impedance variability value based on at least a difference between one of the plurality of measured impedance values and the determined impedance value, wherein the one of the plurality of measured impedance values comprises either a maximum or a minimum impedance value measured during one of the multiple periods of time, and wherein the impedance variability value indicates an expected level of variability for impedance measurements for the electrical path;

determine an impedance threshold value based on the determined impedance value and the impedance variability value;

compare a newly measured impedance value for the electrical path to the impedance threshold value; and indicate a possible condition of the electrical path based on the comparison.

42. A system comprising:

means for obtaining a plurality of measured impedance values for an electrical path that are measured over multiple periods of time, wherein the electrical path comprises a plurality of electrodes for at least one of stimulation or sensing;

means for obtaining a central tendency of the plurality of measured impedance values for the electrical path;

means for determining an impedance value for the electrical path based on the central tendency;

means for determining an impedance variability value based on a difference between at least one of the plurality of measured impedance values and the determined impedance value, wherein the one of the plurality of measured impedance values comprises either a maximum or a minimum impedance value measured during one of the multiple periods of time, and wherein the impedance variability value indicates an expected level of variability for impedance measurements for the electrical path;

means for determining an impedance threshold value based on the determined impedance value and the impedance variability value;

means for comparing a newly measured impedance value for the electrical path to the impedance threshold value; and means for indicating a possible condition of the electrical path based on the comparison.

* * * * *